(12) United States Patent
Candau

(10) Patent No.: US 6,627,180 B2
(45) Date of Patent: Sep. 30, 2003

(54) SYNERGISTICALLY UV-PHOTOPROTECTING COMPOSITIONS COMPRISING MIXED SCREENING AGENTS

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 10/314,195

(22) Filed: Dec. 9, 2002

(65) Prior Publication Data

US 2003/0152532 A1 Aug. 14, 2003

(30) Foreign Application Priority Data

Dec. 7, 2001 (FR) .............................. 01 15860

(51) Int. Cl.$^7$ .............................. A61K 7/42; A61K 7/44; A61K 7/00
(52) U.S. Cl. .............................. 424/59; 424/60; 424/400; 424/401
(58) Field of Search .............................. 424/59, 60, 400, 424/401

(56) References Cited

FOREIGN PATENT DOCUMENTS

| EP | 0 790 243 | A1 | 8/1997 |
|----|-----------|-----|--------|
| EP | 0 893 119 | A1 | 1/1999 |
| EP | 1 046 391 | A2 | 10/2000 |
| EP | 1 133 980 | A2 | 9/2001 |
| EP | 1 219 287 | A2 | 7/2002 |
| GB | 2 303 549 | A | 2/1997 |
| WO | WO 95/22959 | A2 | 8/1995 |

OTHER PUBLICATIONS

French Search Report Issued for FR 01/15860 on Sep. 3, 2002—3 pages.

*Primary Examiner*—Shelley A. Dodson
(74) *Attorney, Agent, or Firm*—Burns, Doane, Swecker & Mathis, L.L.P.

(57) ABSTRACT

Topically applicable cosmetic/dermatological sunscreen compositions well suited for the enhanced UV-photoprotection of human skin and/or hair contain synergistically UV-$A_{PPD}$-enhancing amounts of (a) particulates of at least one insoluble organic UV-screening agent having a particle size ranging from 10 nm to 5 µm, and (b) at least one UV-screening amino-substituted 2-hydroxybenzophenone compound having the following structural formula (I):

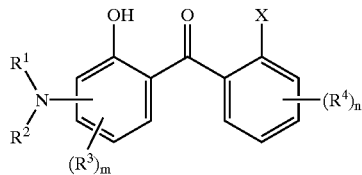

formulated into (c) a topically applicable, cosmetically/dermatologically acceptable vehicle, diluent or carrier therefor.

65 Claims, No Drawings

SYNERGISTICALLY UV-PHOTOPROTECTING COMPOSITIONS COMPRISING MIXED SCREENING AGENTS

CROSS-REFERENCE TO PRIORITY APPLICATION

This application claims priority under 35 U.S.C. §119 of FR-01/15860, filed Dec. 7, 2001, hereby expressly incorporated by reference.

BACKGROUND OF THE INVENTION

1. Technical Field of the Invention

The invention relates to novel cosmetic or dermatological compositions for topical use, in particular for the photoprotection of the skin and/or hair, characterized in that they comprise, in a cosmetically acceptable vehicle, at least:

(a) one insoluble organic UV screening agent with a particle size ranging from 10 nm to 5 μm, as first screening agent, and (b) one specific amino-substituted 2-hydroxybenzophenone derivative, as second screening agent. The combination of these two screening agents results in a synergistic effect being obtained with regard to the sun protection factors UV-APPD conferred.

The invention also relates to their applications in the protection of the skin and hair against the effects of ultraviolet radiation.

2. Description of the Prior Art

It is known that light radiation with wavelengths of between 280 nm and 400 nm makes possible browning of the human epidermis and that rays with wavelengths of between 280 and 320 nm, known under the name of UV-B, cause erythemas and skin burns which may be harmful to the development of natural tanning; this UV-B radiation must therefore be screened out.

It is also known that UV-A rays, with wavelengths of between 320 and 400 nm, which cause browning of the skin, are capable of bringing about a detrimental change in the latter, in particular in the case of sensitive skin or of skin continually exposed to solar radiation. UV-A rays cause in particular a loss in the elasticity of the skin and the appearance of wrinkles, resulting in premature ageing. They promote the triggering of the erythemal reaction or accentuate this reaction in some subjects and can even be the cause of phototoxic or photoallergic reactions. It is therefore desirable also to screen out UV-A radiation.

Numerous cosmetic compositions intended for the photoprotection (UV-A and/or UV-B) of the skin have been provided to date.

The efficacy of antisun compositions is generally expressed by the sun protection factor (SPF), which is expressed mathematically by the ratio of the dose of UV radiation necessary to reach the erythemogenic threshold with the UV screening agent to the dose of UV radiation necessary to reach the erythemogenic threshold without UV screening agent. This factor thus relates to the effectiveness of the protection with respect to erythema, the spectrum of biological action of which is centered in the UV-B region, and consequently describes the protection with respect to this UV-B radiation.

In view of the effects of UV-A radiation on the skin and of the development of numerous compositions comprising combinations of screening agents capable of absorbing UV-B and/or UV-A radiation, specific methods for evaluating protection against UV-A radiation have been developed.

For the characterization of protection with respect to UV-A radiation, the PPD (Persistent Pigment Darkening) method, which measures the color of the skin observed 2 to 4 hours after exposure of the skin to UV-A radiation, is particularly recommended and used. This method was adopted in 1996 by the Japanese Cosmetic Industry Association (JCIA) as official test procedure for the UV-A labeling of products and is frequently used by test laboratories in Europe and the United States (Japan Cosmetic Industry Association Technical Bulletin. Measurement Standards for UVA protection efficacy. Issued Nov. 21, 1995 and effective of Jan. 1, 1996).

The sun protection factor UV-$A_{PPD}$ (UV-$A_{PPD}$ PF) is expressed mathematically by the ratio of the dose of UV-A radiation necessary to reach the pigmentation threshold with the UV screening agent (MPPD$_p$) to the dose of UV-A radiation necessary to reach the pigmentation threshold without UV screening agent (MPPD$_{np}$).

$$UV\text{-}A_{PPD}PF = \frac{MPPD_p}{MPPD_{np}}$$

These antisun compositions exist fairly often in the form of an emulsion of oil-in-water type (that is to say, a cosmetically acceptable vehicle composed of a continuous aqueous dispersing phase and of a noncontinuous oily dispersed phase) which comprises, at various concentrations, one or more conventional, lipophilic and/or hydrophilic, organic screening agents capable of selectively absorbing harmful UV radiation, these screening agents (and their amounts) being selected according to the sun protection factors desired.

Antisun compositions based on amino-substituted 2-hydroxybenzophenone derivatives are known from Patent Applications EP-A-1,046,391 and DE 100 12 408.

SUMMARY OF THE INVENTION

In point of fact, following much research carried out in the abovementioned field of photoprotection, the Applicant Company has discovered, unexpectedly and surprisingly, that the combination, in proportions within well-defined limits, of two specific sunscreens already known per se in the state of the art makes it possible, due to a notable synergistic effect, to obtain antisun compositions exhibiting sun protection factors UV-$A_{PPD}$ which are markedly improved and in any case much higher than those which can be obtained with either of the screening agents used on its own.

This discovery forms the basis of the present invention.

Thus, in accordance with one of the subject-matters of the present invention, novel cosmetic compositions for topical use, in particular for the photoprotection of the skin and/or hair, are now provided, characterized in that they comprise, in a cosmetically acceptable vehicle:

(a) at least one insoluble organic UV screening agent with a particle size ranging from 10 nm to 5 μm, as first screening agent, and (b) at least one amino-substituted 2-hydroxy-benzophenone derivative of formula (I) which will be defined later, as second screening agent.

Another subject-matter of the present invention is the use of such compositions in the manufacture of cosmetic compositions intended for the protection of the skin and/or hair against ultraviolet radiation, in particular solar radiation.

Another subject-matter of the present invention is the use of an amino-substituted 2-hydroxybenzophenone derivative of formula (I) which will be defined later in the manufacture of cosmetic or dermatological compositions intended for the protection of the skin and/or hair against ultraviolet radiation, in particular solar radiation, comprising at least one insoluble organic UV screening agent with a particle size ranging from 10 nm to 5 µm, for the purpose of producing a synergistic effect with regard to the sun protection factors UV-$A_{PPD}$ conferred.

The term "insoluble UV screening agent" within the meaning of the present invention is understood to mean any organic or inorganic UV screening agent having a solubility in water of less than 0.1% by weight and a solubility of less than 1% by weight in the majority of organic solvents, such as liquid paraffin, fatty alcohol benzoates and fatty acid triglycerides, for example Miglyol® 812 sold by Dynamit Nobel. This solubility, defined at 70° C. as the amount of product in solution in the solvent at equilibrium with an excess of solid in suspension, can easily be evaluated in the laboratory.

Other characteristics, aspects and advantages of the present invention will become apparent on reading the detailed description which will follow.

DETAILED DESCRIPTION OF BEST MODE AND SPECIFIC/PREFERRED EMBODIMENTS OF THE INVENTION

Generally, the insoluble UV screening agent and the amino-substituted 2-hydroxybenzophenone derivative are present in the said compositions in a proportion producing a synergistic activity with regard to the sun protection factors UV-$A_{PPD}$ conferred.

The insoluble organic UV screening agents according to the invention have a mean particle size which varies from 10 to 5 µm and more preferably from 10 nm to 2 µm and more particularly from 20 nm to 2 µm.

The insoluble organic screening agents according to the invention can be brought to the desired particulate form by any ad hoc means, such as, in particular, dry milling or milling in a solvent medium, sieving, atomization, micronization or spraying.

The insoluble organic screening agents according to the invention in the micronized form can be obtained in particular by a process of milling an insoluble organic UV screening agent in the form of coarse particles in the presence of an appropriate surfactant which makes it possible to improve the dispersion of the particles thus obtained in cosmetic formulations.

An example of a process for the micronization of insoluble organic screening agents is disclosed in Applications GB-A-2 303 549 and EP-A-893 119, which form an integral part of the description. The milling device used according to these documents can be an airjet mill, bead mill, vibration mill or hammer mill and preferably a mill with high-speed stirring or an impact mill and more particularly a rotary bead mill, a vibrating mill, a tube mill or a rod mill.

According to this specific process, use is made, as surfactants for the milling of the said screening agents, of alkypolyglucosides with the structure $C_nH_{2n+1}O(C_6H_{10}O_5)_xH$ in which n is an integer from 8 to 16 and x is the mean degree of polymerization of the $(C_6H_{10}O_5)$ unit and varies from 1.4 to 1.6. They can be chosen from $C_1$–$C_2$ esters of a compound with the structure $C_nH_{2n+1}O(C_6H_{10}O_5)_xH$ and more specifically an ester obtained by reaction of a $C_1$–$C_{12}$ carboxylic acid, such as formic, acetic, propionic, butyric, sulfosuccinic, citric or tartaric acid, with one or more free OH functional groups on the glucoside unit $(C_6H_{10}O_5)$. The said surfactants are generally used at a concentration ranging from 1 to 50% by weight and more preferably from 5 to 40% by weight with respect to the insoluble screening agent in its micronized form.

The insoluble organic UV screening agents in accordance with the invention can be chosen in particular from organic UV screening agents of the oxalanilide type, of the triazine type, of the benzotriazole type; of the vinyl amide type; of the cinnamamide type; of the type comprising one or more benzazole and/or benzofuran or benzothiophene groups or of the indole type; of the aryl vinylene ketone type; of the phenylenebis(benzoxazinone) derivative type; or of the acrylonitrile amide, sulfonamide or carbamate derivative type.

In the sense in which it is used in the present invention, the term benzazole simultaneously encompasses benzothiazoles, benzoxazoles and benzimidazoles.

Mention may be made, among UV screening agents of the oxalanilide type in accordance with the invention, of those corresponding to the structure:

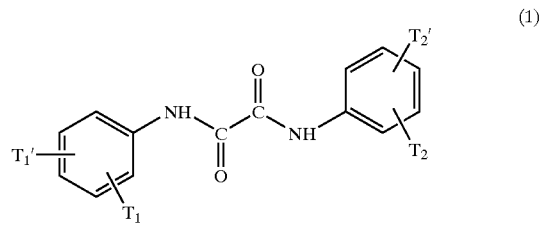

(1)

in which $T_1$, $T'_1$, $T_2$ and $T'_2$, which are identical or different, denote an hydrogen atom, a $C_1$–$C_8$ alkyl radical or a $C_1$–$C_8$ alkoxy radical. These compounds are disclosed in Patent Application WO 95/22959.

Mention may be made, as examples, of the commercial products Tinuvin 315 and Tinuvin 312, sold by Ciba-Geigy, with the respective structures:

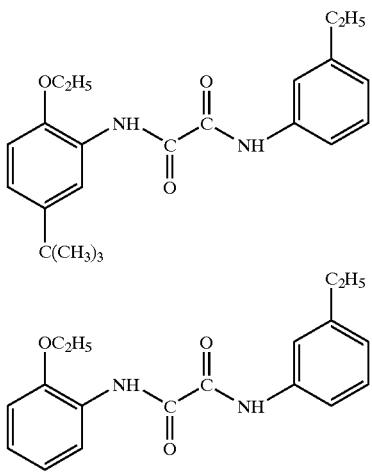

Mention may also be made, among insoluble UV screening agents of the triazine type in accordance with the invention, of those corresponding to the following formula (2):

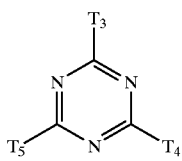

(2)

in which $T_3$, $T_4$ and $T_5$ are independently phenyl, phenoxy or pyrrolo, in which the phenyl, phenoxy or pyrrolo groups are unsubstituted or substituted by one, two or three substituents chosen from OH, $C_1$–$C_{18}$ alkyl or $C_1$–$C_{18}$ alkoxy, $C_1$–$C_{18}$ carboxyalkyl, $C_5$–$C_8$ cycloalkyl, a methylbenzylidenecamphor group, a —(CH═CH)$_n$(CO)—OT$_6$ group, with $T_6$ either $C_1$–$C_{18}$ alkyl or cinnamyl, and n has the value 0 or 1.

These compounds are disclosed in WO 97/03642, GB 2 286 774, EP-743 309, WO 98/22447 and GB 2 319 523 (which form an integral part of the content of the description).

Mention may also be made, among UV screening agents of the triazine type in accordance with the invention, of insoluble s-triazine derivatives carrying benzalmalonate and/or phenylcyanoacrylate groups, such as those disclosed in Application EP-A-0 790 243 (which forms an integral part of the content of the description).

Mention will more particularly be made, among these insoluble UV screening agents of the triazine type, of the following compounds:

2,4,6-tris(diethyl 4'-aminobenzalmalonate)-s-triazine,
2,4,6-tris(diisopropyl 4'-aminobenzalmalonate)-s-triazine,
2,4,6-tris(dimethyl 4'-aminobenzalmalonate)-s-triazine,
2,4,6-tris(ethyl α-cyano-4-aminocinnamate)-s-triazine.

Mention may also be made, among UV screening agents of the triazine type in accordance with the invention, of insoluble s-triazine derivatives carrying benzotriazole and/or benzothiazole groups, such as those disclosed in Application WO 98/25922 (which forms an integral part of the content of the description).

Mention may more particularly be made, among these compounds, of:

2,4,6-tris[(3'-(benzotriazol-2-yl)-2'-hydroxy-5'-methyl) phenylamino]-s-triazine,
2,4,6-tris[(3'-(benzotriazol-2-yl)-2'-hydroxy-5'-tert-octyl) phenylamino]-s-triazine.

Mention may be made, among insoluble organic UV screening agents of the benzotriazole type in accordance with the invention, of those of following formula (3) as disclosed in Application WO 95/22959 (which forms an integral part of the content of the description):

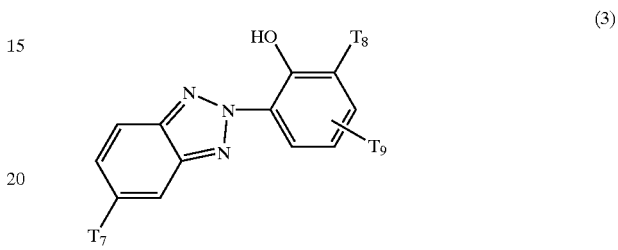

(3)

in which $T_7$ denotes a hydrogen atom or a $C_1$–$C_{18}$ alkyl radical; $T_8$ and $T_9$, which are identical or different, denote a $C_1$–$C_{18}$ alkyl radical optionally substituted by a phenyl.

Mention may be made, as examples of compounds of formula (3), of the commercial products Tinuvin 328, 320, 234 and 350 from Ciba-Geigy, with the following structures:

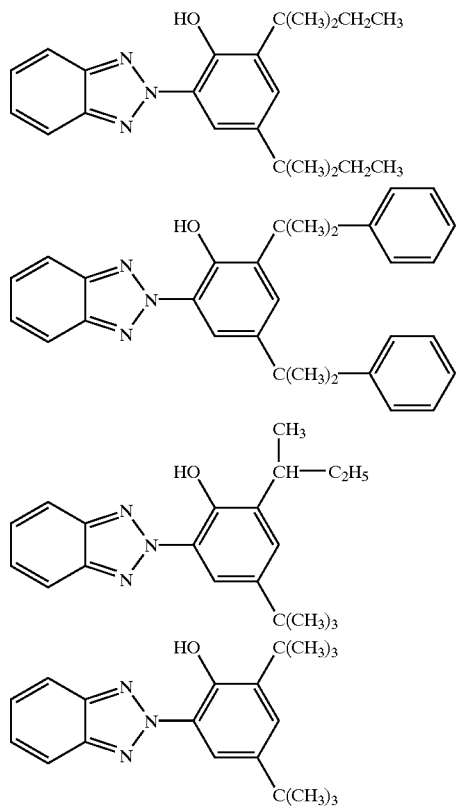

Mention may be made, among insoluble organic UV screening agents of the benzotriazole type in accordance with the invention, of the compounds as disclosed in U.S. Pat. Nos. 5,687,521, 5,373,037 and 5,362,881 and in particular [2,4'-dihydroxy-3-(2H-benzotriazol-2-yl)-5-(1,1,3,3-tetramethylbutyl)-2'-(n-octoxy)-5'-benzoyl]diphenylmethane, sold under the name Mixxim PB30 by Fairmount Chemical, with the structure:

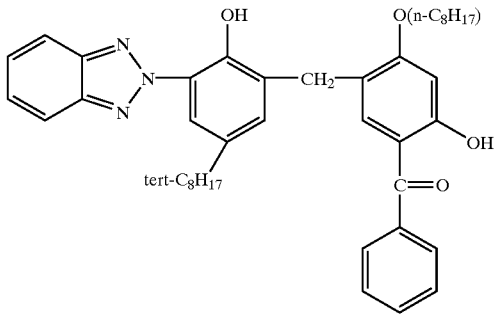

Mention may be made, among insoluble organic UV screening agents of the benzotriazole type in accordance with the invention, of methylenebis-(hydroxyphenylbenzotriazole) derivatives with the following structure:

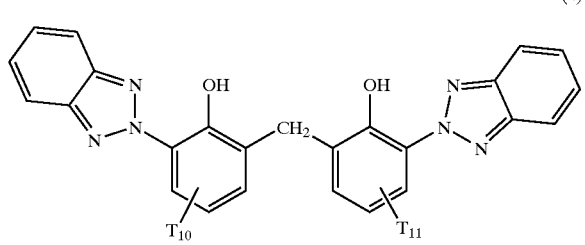

(4)

in which the $T_{10}$ and $T_{11}$ radicals, which are identical or different, denote a $C_1$–$C_{18}$ alkyl radical which can be substituted by one or more radicals chosen from a $C_1$–$C_4$ alkyl radical, a $C_5$–$C_{12}$ cycloalkyl radical or an aryl residue. These compounds are known per se and are disclosed in U.S. Pat. Nos. 5,237,071, 5,166,355, GB-A-2 303 549, DE 197 26 184 and EP-A-893 119 (which form an integral part of the description).

In the formula (4) defined above: the $C_1$–$C_{18}$ alkyl groups can be linear or branched and are, for example, methyl, ethyl, n-propyl, isopropyl, n-butyl, isobutyl, tert-butyl, tert-octyl, n-amyl, n-hexyl, n-heptyl, n-octyl, isooctyl, n-nonyl, n-decyl, n-undecyl, n-dodecyl, tetradecyl, hexadecyl or octadecyl; the $C_5$–$C_{12}$ cycloalkyl groups are, for example, cyclopentyl, cyclohexyl or cyclooctyl; and the aryl groups are, for example, phenyl or benzyl.

Preference is more particularly given, among the compounds of formula (4), to those with the following structures:

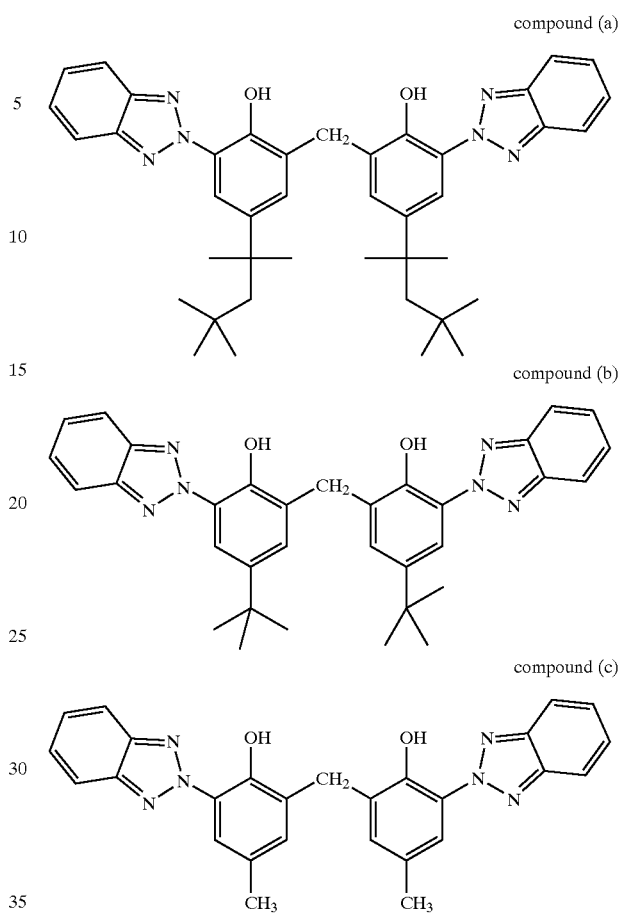

Compound (a), with the nomenclature 2,2'-methylenebis[6-(2H-benzotriazol-2-yl)-4-(1,1,3,3-tetramethylbutyl)phenol], is sold in the micronized form under the name Tinosorb M by Ciba Specialty Chemicals.

Compound (c), with the nomenclature 2,2'-methylenebis[6-(2H-benzotriazol-2-yl)-4-methyl-phenol], is sold in the solid form under the name Mixxim BB/200 by Fairmount Chemical.

Mention may be made, among insoluble organic screening agents of the vinyl amide type, of, for example, the compounds with the following formula which are disclosed in Application WO 95/22959 (which forms an integral part of the content of the description):

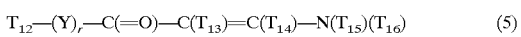

$$T_{12}\text{—}(Y)_r\text{—}C(\!=\!O)\text{—}C(T_{13})\!=\!C(T_{14})\text{—}N(T_{15})(T_{16}) \qquad (5)$$

in which $T_{12}$ is a $C_1$–$C_{18}$, preferably $C_1$–$C_5$, alkyl radical or a phenyl group optionally substituted by one, two or three radicals chosen from OH, a $C_1$–$C_{18}$ alkyl radical, a $C_1$–$C_8$ alkoxy radical, or a group —C(=O)—OT$_{17}$ where T$_{17}$ is a $C_1$–$C_{18}$ alkyl; $T_{13}$, $T_{14}$, $T_{15}$ and $T_{16}$, which are identical or different, denote a $C_1$–$C_{18}$, preferably $C_1$–$C_5$, alkyl radical or a hydrogen atom; Y is N or O and r has the value 0 or 1.

Mention will more particularly be made, among these compounds, of:
4-octylamino-3-penten-2-one;
ethyl 3-octylamino-3-butenoate;
3-octylamino-1-phenyl-2-buten-1-one;
3-dodecylamino-1-phenyl-2-buten-1-one.

Mention may also be made, among insoluble organic screening agents of the cinnamamide type in accordance with the invention, of the compounds as disclosed in Application WO 95/22959 (which forms an integral part of the content of the description) and corresponding to the following structure:

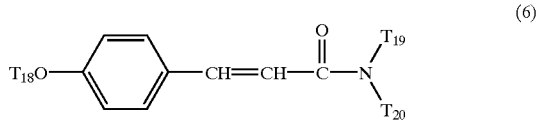

(6)

in which $OT_{18}$ is a hydroxyl or $C_1$–$C_4$ alkoxy radical, preferably a methoxy or ethoxy radical; $T_{19}$ is hydrogen or $C_1$–$C_4$ alkyl, preferably methyl or ethyl; $T_{20}$ is a —(CONH)$_s$-phenyl group where s has the value 0 or 1 and the phenyl group can be substituted by one, two or three groups chosen from OH, $C_1$–$C_{18}$ alkyl, $C_1$–$C_8$ alkoxy, or a —C(=O)—$OT_{21}$ group where $T_{21}$ is a $C_1$–$C_{18}$ alkyl and more preferably $T_{21}$ is a phenyl, 4-methoxyphenyl or phenylaminocarbonyl group.

Mention may also be made of cinnamamide dimers, such as those disclosed in U.S. Pat. No. 5,888,481, such as, for example, the compound with the structure:

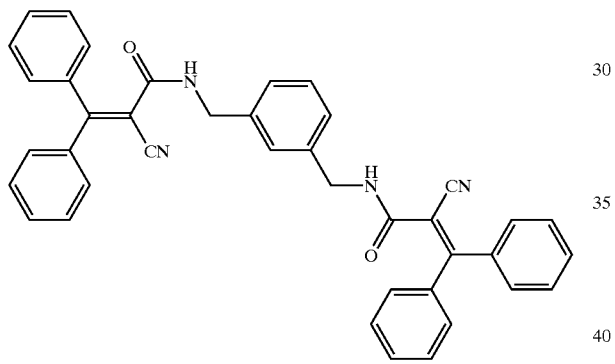

Mention may be made, among insoluble organic screening agents of the benzazole type, of those corresponding to one of the following formulae:

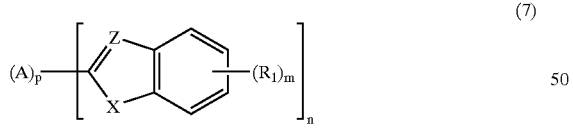

(7)

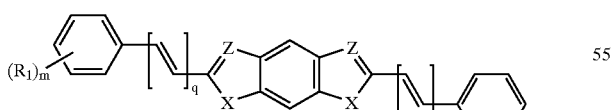

(8)

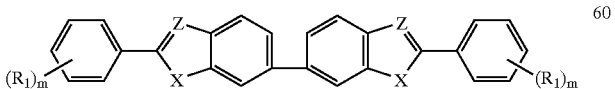

(9)

in which each of the X symbols independently represents an oxygen or sulfur atom or an $NR_2$ group, each of the Z symbols independently represents a nitrogen atom or a CH group, each of the $R_1$ symbols independently represents an OH group, a halogen atom, a linear or branched $C_{1-8}$ alkyl group, optionally comprising a silicon atom, or a linear or branched $C_{1-8}$ alkoxy group, each of the numbers m independently has the value 0, 1 or 2, n represents an integer between 1 and 4 inclusive, p is equal to 0 or 1, each of the numbers q is independently equal to 0 or 1, each of the $R_2$ symbols independently represents a hydrogen atom or a benzyl or linear or branched $C_{1-8}$ alkyl group, optionally comprising a silicon atom, A represents a radical with a valency n chosen from those of formulae:

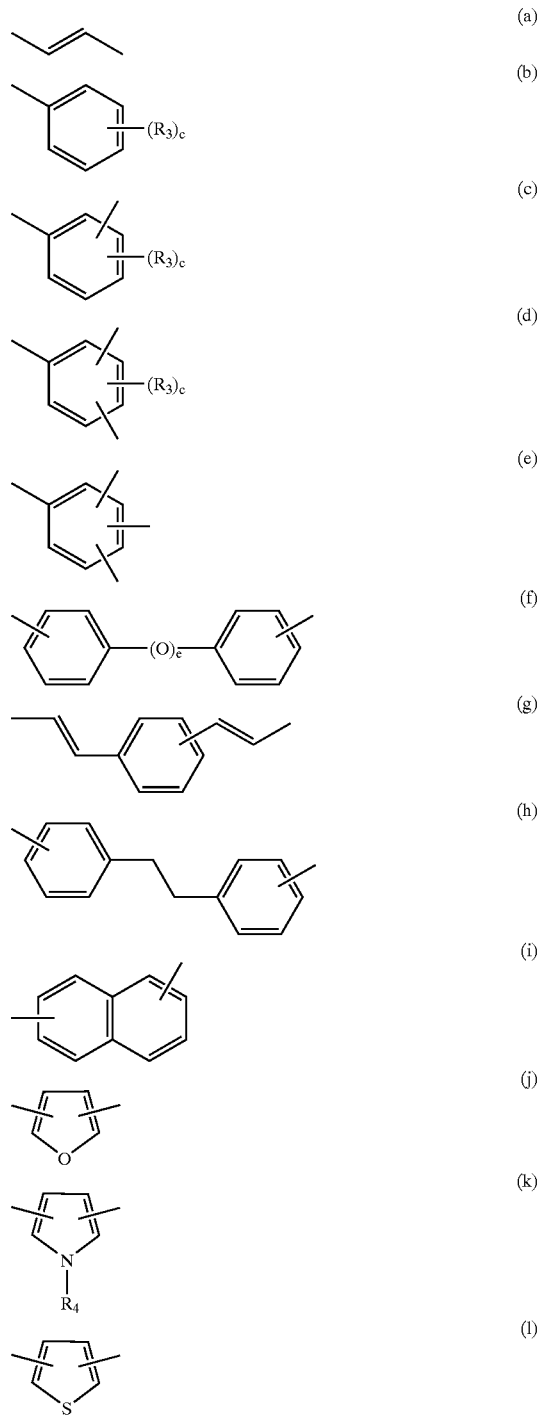

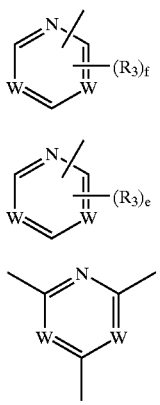

in which W denotes N or CH; each of the $R_3$ symbols independently represents a halogen atom or a linear or branched $C_{1-4}$ alkyl or alkoxy group or a hydroxyl group, $R_4$ represents a hydrogen atom or a linear or branched $C_{1-4}$ alkyl group, c=0–4, d=0–3, e=0 or 1 and f=0–2.

These compounds are disclosed in particular in Patents DE 676 103 and CH 350 763, U.S. Pat. Nos. 5,501,850, 5,961,960, Patent Application EP 0 669 323, U.S. Pat. Nos. 5,518,713, 2,463,264, the paper in J. Am. Chem. Soc., 79, 5706–5708, 1957, the paper in J. Am. Chem. Soc., 82, 609–611, 1960, Patent Application EP 0 921 126 and Patent Application EP 712 855.

Mention may be made, as examples of preferred compounds of formula (7) of the family of the 2-arylbenzazoles, of 2-(benzoxazol-2-yl)-4-methyl-phenol, 2-(1H-benzimidazol-2-yl)-4-methoxyphenol or 2-(benzothiazol-2-yl)phenol, it being possible for these compounds to be prepared, for example, according to the processes disclosed in Patent CH 350 763.

Mention will be made, as examples of preferred compounds of formula (7) of the family of the benzimidazolylbenzazoles, of 2,2'-bisbenzimidazole, 5,5',6,6'-tetramethyl-2,2'-bisbenzimidazole, 5,5'-dimethyl-2,2'-bisbenzimidazole, 6-methoxy-2,2'-bisbenzimidazole, 2-(1H-benzimidazol-2-yl)-benzothiazole, 2-(1H-benzimidazol-2-yl)benzoxazole and N, N'-dimethyl-2,2'-bisbenzimidazole, it being possible for these compounds to be prepared according to the procedures disclosed in U.S. Pat. Nos. 5,961,960 and 2,463,264.

Mention will be made, as examples of preferred compounds of formula (7) of the family of the phenylenebenzazoles, of 1,4-phenylenebis(2-benzoxazolyl), 1,4-phenylenebis(2-benzimidazolyl), 1,3-phenylenebis(2-benzoxazolyl), 1,2-phenylene-bis(2-benzoxazolyl), 1,2-phenylenebis(benzimidazolyl), 1,4-phenylenebis(N-(2-ethylhexyl)-2-benzimidazolyl) and 1,4-phenylenebis(N-trimethylsilylmethyl-2-benzimida-zolyl), it being possible for these compounds to be prepared according to the procedures disclosed in U.S. Pat. No. 2,463,264 and in the publications J. Am. Chem. Soc., 82, 609 (1960) and J. Am. Chem. Soc., 79, 15 5706–5708 (1957).

Mention will be made, as examples of preferred compounds of formula (7) of the family of the benzofuranylbenzoxazoles, of 2-(2-benzofuranyl)-benzoxazole, 2-(benzofuranyl)-5-methylbenzoxazole and 2-(3-methyl-2-benzofuranyl)benzoxazole, it being possible for these compounds to be prepared according to the procedures disclosed in U.S. Pat. No. 5,518,713.

Mention may be made, as preferred compounds of formula (8), of, for example, 2,6-diphenyl-1,7-di-hydrobenzo[1,2-d ;4,5-d']diimidazole, corresponding to the formula

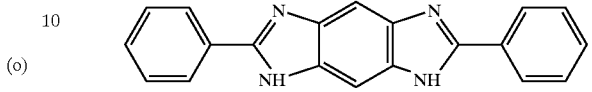

or 2,6-distyryl-1,7-dihydrobenzo[1,2-d;4,5-d']di-imidazole or 2,6-di(p-tert-butylstyryl)-1,7-dihydro-benzo[1,2-d;4,5-d']diimidazole, which compounds can be prepared according to Application EP 0 669 323.

Mention may be made, as preferred compound of formula (9), of 5,5'-bis(2-phenylbenzimidazole) of formula:

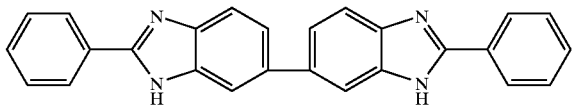

the preparation of which is described in J. Chim. Phys., 64, 1602 (1967).

Preference is very particularly given, among these insoluble organic compounds which screen out UV radiation, to 2-(1H-benzimidazol-2-yl)benzoxazole, 6-methoxy-2,2'-bisbenzimidazole, 2-(1H-benzimidazol-2-yl)benzothiazole, 1,4-phenylenebis(2-benzoxazolyl), 1,4-phenylenebis(2-benzimidazolyl), 1,3-phenylene-bis(2-benzoxazolyl), 1,2-phenylenebis(2-benzoxazolyl), 1,2-phenylenebis(2-benzimidazolyl) and 1,4-phenylene-bis(N-trimethylsilylmethyl-2-benzimidazolyl).

Mention may be made, among insoluble organic screening agents of the aryl vinylene ketone type, of those corresponding to either of the following formulae (10) and (11):

(10)

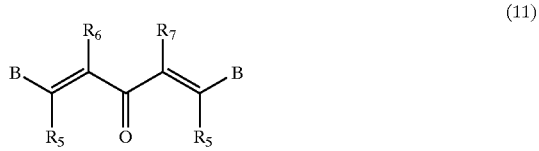

(11)

in which:

n'=1 or 2,

B, in the formula (10) when n'=1 or in the formula (11), is an aryl radical chosen from the following formulae (a') to (d') or, in the formula (10) when n'=2, is a radical chosen from the following formulae (e') to (h'):

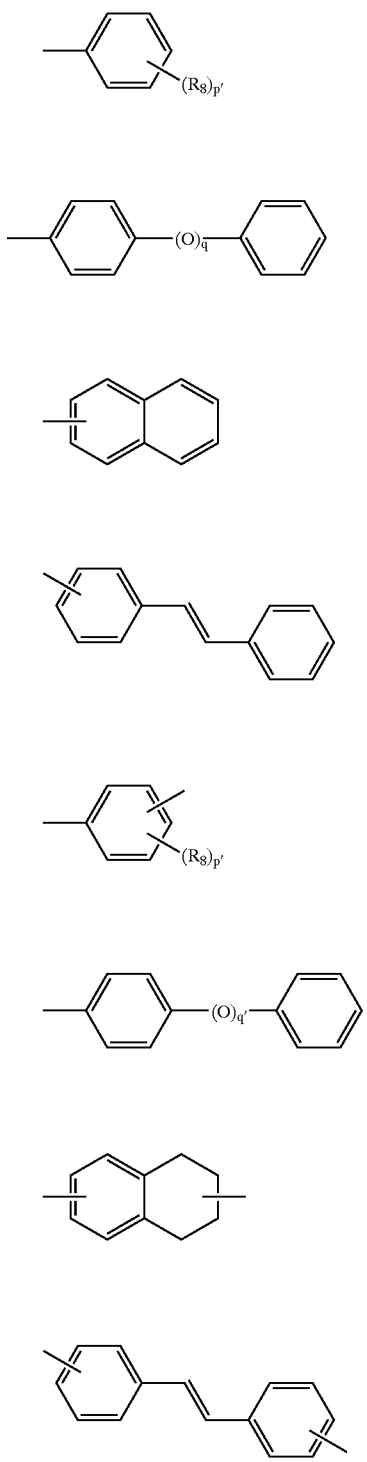

(a')

(b')

(c')

(d')

(e')

(f')

(g')

(h')

in which:

each of the $R_8$ symbols independently represents an OH group, a halogen atom, a linear or branched $C_{1-6}$ alkyl group optionally comprising a silicon atom, a linear or branched $C_{1-6}$ alkoxy group optionally comprising a silicon atom, a linear or branched $C_{1-5}$ alkoxycarbonyl group, or a linear or branched $C_{1-6}$ alkylsulfonamide group optionally comprising a silicon atom or an amino acid functional group, p' represents an integer between 0 and 4 inclusive, q' represents 0 or 1, $R_5$ represents hydrogen or an OH group, $R_6$ represents hydrogen, a linear or branched $C_{1-6}$ alkyl group optionally comprising a silicon atom, a cyano group, a $C_{1-6}$ alkylsulfonyl group or a phenylsulfonyl group, $R_7$ represents a linear or branched $C_{1-6}$ alkyl group optionally comprising a silicon atom or a phenyl group which can form a bicycle and which is optionally substituted by one or two $R_4$ radicals, or $R_6$ and $R_7$ together form a monocyclic, bicyclic or tricyclic $C_{2-10}$ hydrocarbonaceous residue, optionally interrupted by one or more nitrogen, sulfur and oxygen atoms and which can comprise another carbonyl, and optionally substituted by a linear or branched $C_1$–$C_8$ alkylsulfonamide group, and optionally comprising a silicon atom or an amino acid functional group; provided that, when n'=1, $R_6$ and $R_7$ do not form a camphor nucleus.

Mention may be made, as examples of compounds of formula (10) in which n'=1, which are insoluble, which screen out UV radiation and which have a mean particle size of between 10 nm and 5 µm, of the following families:

compounds of the styryl ketone type as disclosed in Application JP 04 134 042, such as 1-(3,4-dimethoxy-5 phenyl)-4,4-dimethylpent-1-en-3-one:

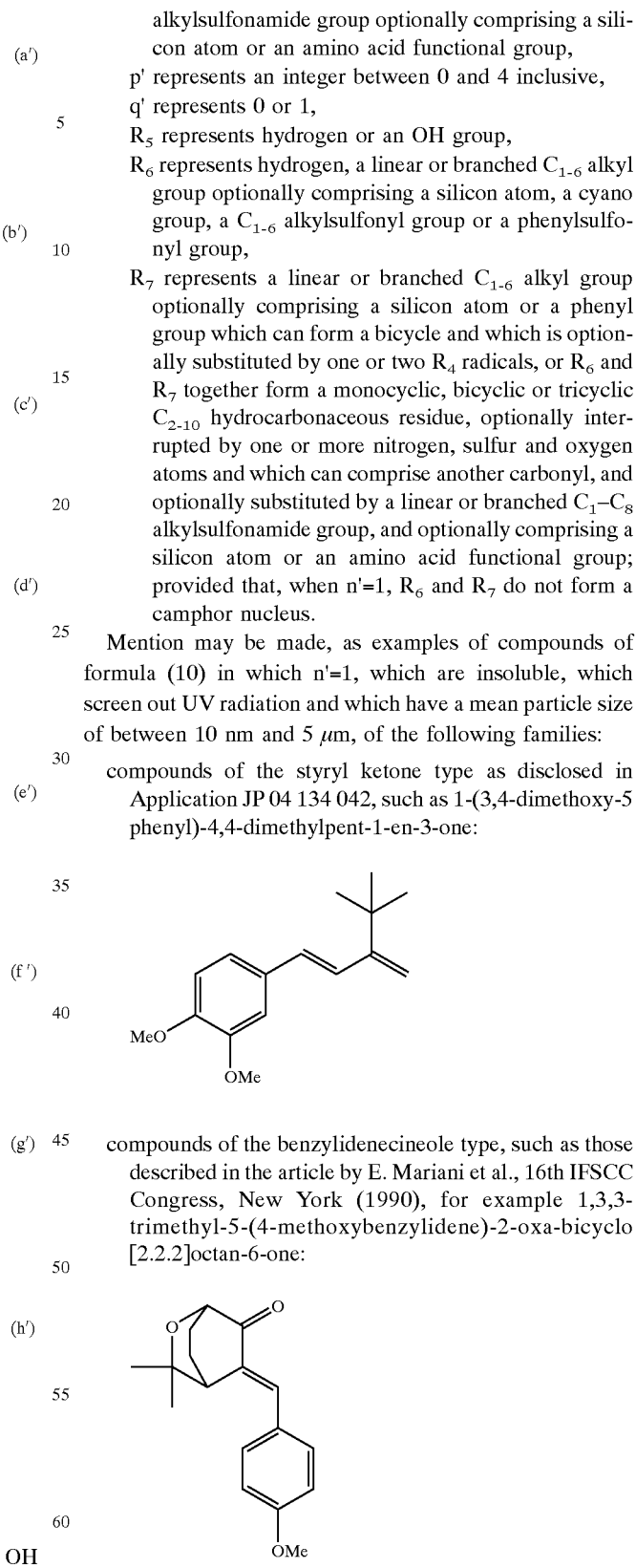

compounds of the benzylidenecineole type, such as those described in the article by E. Mariani et al., 16th IFSCC Congress, New York (1990), for example 1,3,3-trimethyl-5-(4-methoxybenzylidene)-2-oxa-bicyclo[2.2.2]octan-6-one:

compounds of the benzylidenechromanone type, such as those disclosed in Application JP 04 134 043, for example 3-(4-methoxybenzylidene)-2,3,4a,8a-tetrahydro-chromen-4-one:

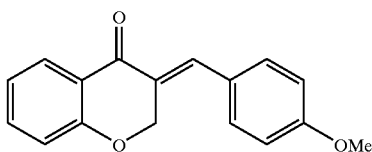

compounds of the benzylidenethiochromanone type, such as those disclosed in Application JP 04 134 043, for example 3-(4-methoxybenzylidene)-2,3,4a,8a-tetrahydro-chromen-4-thione:

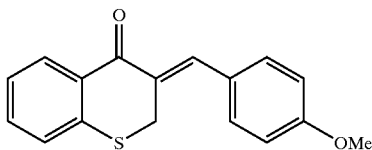

compounds of the benzylidenequinuclidinone type, such as those disclosed in Application EP 0 576 974, for example 4-methoxybenzylidene-1-azabicyclo[2.2.2]octan-3-one:

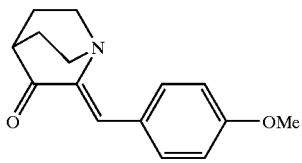

compounds of the benzylidenecycloalkanone type, such as those disclosed in Application FR 2 395 023, for example 2-(4-methoxybenzylidene)cyclopentanone and 2-(4-methoxybenzylidene)cyclohexanone:

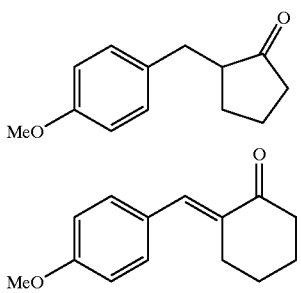

compounds of the benzylidenehydantoin type, such as those disclosed in Application JP 01 158 090, for example 5-(3,4-dimethoxybenzylidene)imidazolidine-2,4-dione:

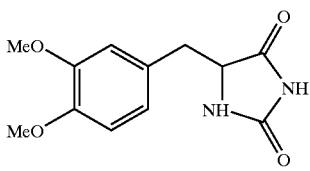

compounds of the benzylideneindanone type, such as those disclosed in Application JP 04 134 043, for example 2-(4-methoxybenzylidene)indan-1-one:

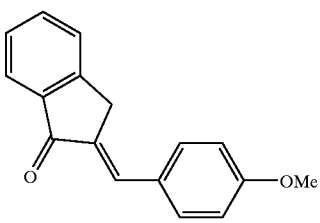

compounds of the benzylidenetetralone type, such as those disclosed in Application JP 04 134 043, for example 2-(4-methoxybenzylidene)-3,4-dihydro-2H-naphthalen-1-one

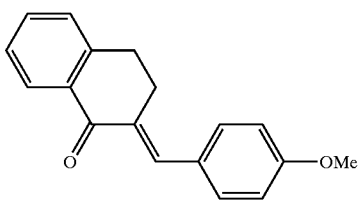

compounds of the benzylidenefuranone type, such as those disclosed in Application EP 0 390 683, for example 4-(4-methoxybenzylidene)-2,2,5,5-tetramethyl-dihydrofuran-3-one:

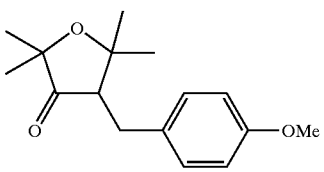

compounds of the benzylidenebenzofuranone type, such as those disclosed in Application JP 04 134 041, for example 2-benzylidenebenzofuran-3-one:

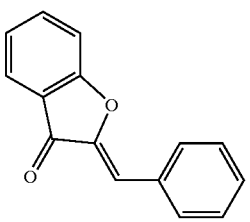

compounds of the benzylideneindanedione type, such as 2-(3,5-di(tert-butyl)-4-hydroxybenzylidene)indane-1,3-dione:

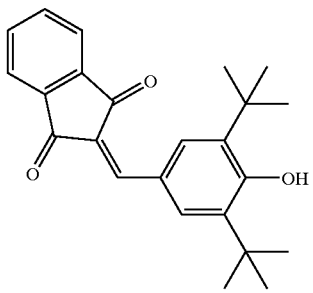

compounds of the benzylidenebenzothiofuranone type, such as those disclosed in Application JP 04,134,043, for example 2-benzylidenebenzo[b]thiophen-3-one:

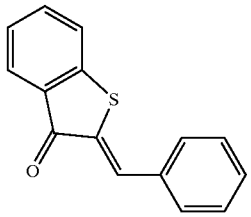

compounds of the benzylidenebarbituric type, such as 5-(4-methoxybenzylidene)-1,3-dimethylpyrimidine-2,4,6-trione:

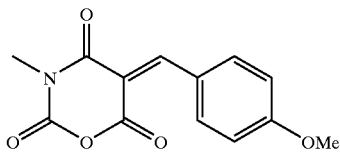

compounds of the benzylidenepyrazolone type, such as 4-(4-methoxybenzylidene)-5-methyl-2-phenyl-2,4-dihydro-pyrazol-3-one:

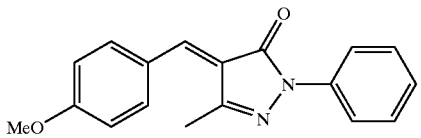

compounds of the benzylideneimidazolone type, such as 5-(4-methoxybenzylidene)-2-phenyl-3,5-dihydroimidazol-4-one:

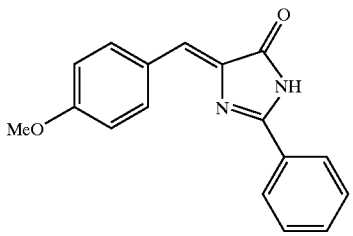

compounds of the chalcone type, such as 1-(2-hydroxy-4-methoxyphenyl)-3-phenylpropenone:

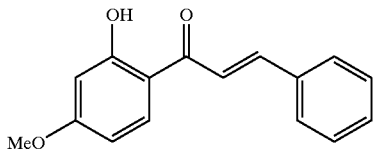

benzylidenone compounds as disclosed in the document FR 2 506 156, for example 3-hydroxy-1-(2-hydroxy-4-methoxyphenyl)-3-phenylpropenone:

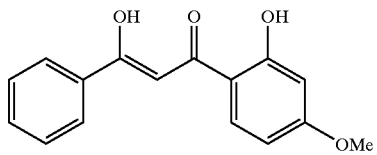

Mention may be made, as examples of compounds of formula (10) in which n'=2, which are insoluble, which screen out UV radiation and which have a mean particle size of between 10 nm and 5 $\mu$m, of the following families:

compounds of the phenylenebis(methylidenenorcamphor) type as disclosed in the document EP 0 693 471, for example 1,4-phenylenebis{3-methylidenebicyclo[2.2.1]-heptan-2-one}:

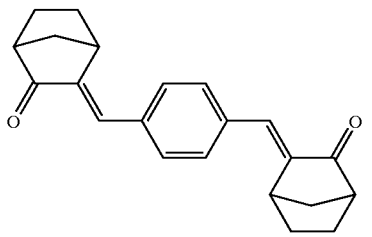

compounds of the phenylenebis(methylidenecamphor) type as disclosed in the document FR 2 528 420, for example 1,4-phenylenebis{3-methylidene-1,7,7-trimethylbicyclo[2.2.1]heptan-2-one}:

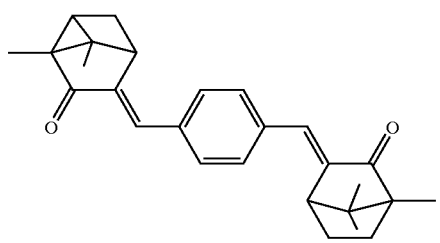

or 1,3-phenylenebis{3-methylidene-1,7,7-trimethyl-bicyclo[2.2.1]heptan-2-one}:

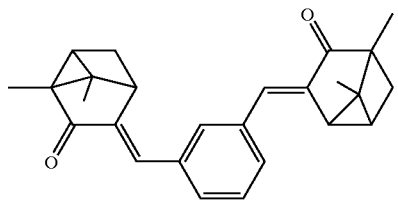

compounds of the phenylenebis(methylidenecamphor-sulfonamide) type, such as those disclosed in the document FR 2 529 887, for example 1,4-phenylene-bis{3,3'-methylidenecamphor-10,10'-ethylsulfonamide or -(2-ethylhexyl)sulfonamide}:

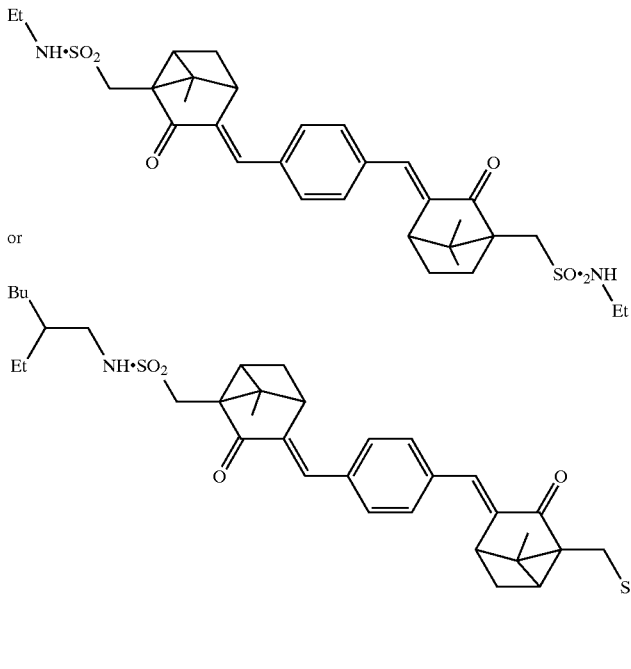

or compounds of the phenylenebis(methylidenecineole) type as described in the paper by E. Mariani et al., 16th IFSCC Congress, New York (1990), for example 1,4-phenylenebis{5-methylidene-3,3-dimethyl-2-oxa-bicyclo[2.2.2]octan-6-one}:

compounds of the phenylenebis(methylideneketo-tricyclodecane) type as disclosed in Application EP 0 694 521, such as 1,4-phenylenebis(octahydro-4,7-methano-6-inden-5-one):

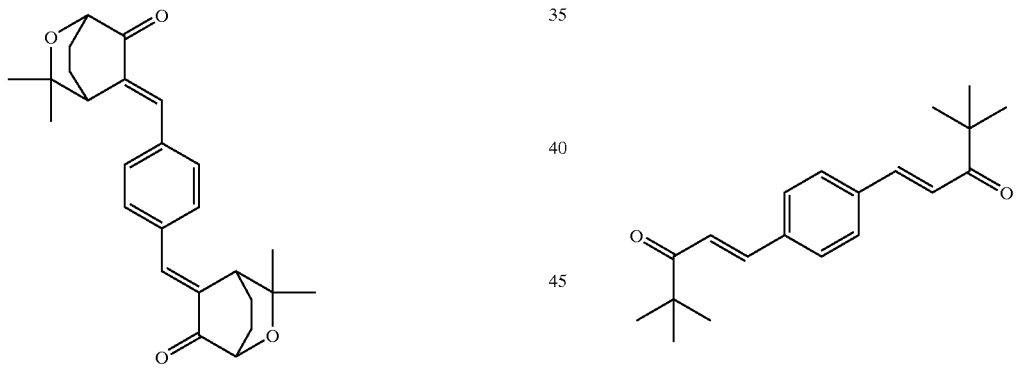

compounds of the phenylenebis(alkylene ketone) type, such as those disclosed in Application JP 04 134 041, for example 1,4-phenylenebis(4,4-dimethylpent-1-en-3-one):

compounds of the phenylenebis(methylidenefuranone) type as disclosed in Application FR 2 638 354, for example 1,4-phenylenebis(4-methylidene-2,2,5,5-tetramethyldihydrofuran-3-one):

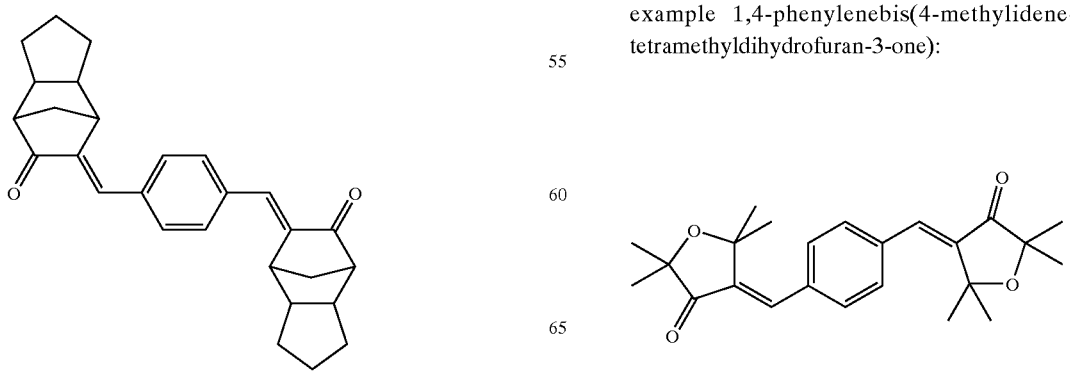

compounds of the phenylenebis(methylidenequinuclidinone) type, such as those disclosed in Application EP 0 714 880, for example 1,4-phenylene-bis{2-methylidene-1-azabicyclo[2.2.2]octan-3-one}:

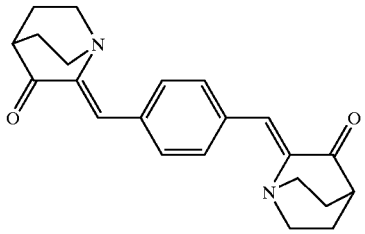

Mention may be made, as compounds of formula (11), of the following families:

compounds of the bis(benzylidene)cycloalkanone type, such as 2,5-di(benzylidene)cyclopentanone:

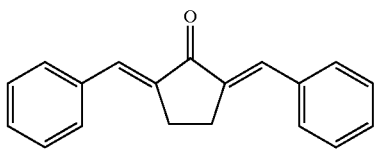

compounds of the γ-pyrone type as disclosed in the document JP 04 290 882, for example 2,6-bis(3,4-dimethoxyphenyl)pyran-4-one:

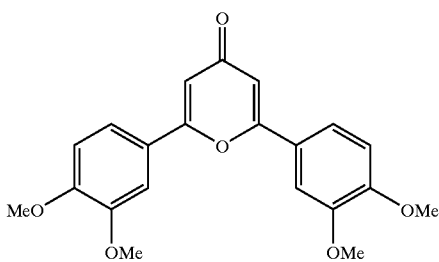

Preference is very particularly given, among these insoluble organic compounds which screen out UV radiation of the aryl vinylene ketone type, to the compounds of formula (10) in which n'=2.

Mention may be made, among insoluble organic screening agents of the phenylenebis(benzoxazinone) type, of those corresponding to the following formula (12):

(12)

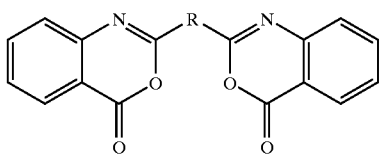

with R representing a divalent aromatic residue chosen from the following formulae (e″) to (h″):

(e″)

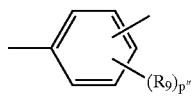

(f″)

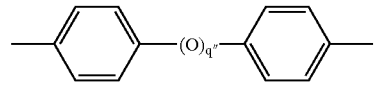

(g″)

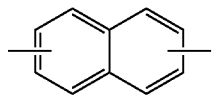

(h″)

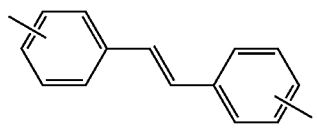

in which:
each of the $R_9$ symbols independently represents an OH group, a halogen atom, a linear or branched $C_{1-6}$ alkyl group optionally comprising a silicon atom, a linear or branched $C_{1-6}$ alkoxy group optionally comprising a silicon atom, a linear or branched $C_{1-5}$ alkoxycarbonyl group, or a linear or branched $C_{1-6}$ alkylsulfonamide group optionally comprising a silicon atom or an amino acid functional group, p″ represents an integer between 0 and 4 inclusive, q″ represents 0 or 1.

Mention may be made, as examples of compounds of formula (12), which are insoluble, which screen out UV radiation and which have a mean particle size of between 10 nm and 5 μm, of the following derivatives:

2,2′-p-phenylenebis(3,1-benzoxazin-4-one), commercial product Cyasorb UV-3638 from Cytec, 2,2′-(4,4′-biphenylene)bis(3,1-benzoxazin-4-one), 2,2′-(2,6-naphthylene)bis(3,1-benzoxazin-4-one).

Mention may be made, among insoluble organic screening agents of the acrylonitrile amide, sulfonamide or carbamate derivative type, of those corresponding to the following formula (13):

(13)

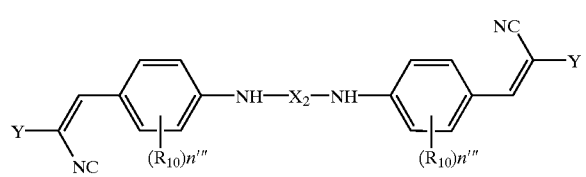

in which:
$R_{10}$ represents a linear or branched $C_{1-8}$ alkyl group, n‴ has the value 0, 1 or 2, $X_2$ represents a divalent radical of formula —(C=O)—$R_{11}$—(C=O)—, —$SO_2$—$R_{11}$—$SO_2$— or —(C=O)—O—$R_{11}$—O—(C=O)—, Y represents a —(C=O)—$R_{12}$ or —$SO_2R_{13}$ radical, $R_{11}$ represents a single bond or a linear or branched, divalent $C_1$–$C_{30}$ alkylene or $C_3$–$C_{30}$ alkenylene radical which can carry one or more hydroxyl substituents and which can comprise, in the carbonaceous chain, one or more heteroatoms chosen from oxygen, nitrogen and silicon atoms, $R_{12}$ represents an —$OR_{14}$ or —$NHR_{14}$ radical, $R_{13}$ represents a linear or branched $C_1$–$C_{30}$ alkyl radical or a phenyl ring which is unsubstituted or substituted by $C_1$–$C_4$ alkyl or alkoxy radicals, $R_{14}$ represents a linear or branched $C_1$–$C_{30}$ alkyl or $C_3$–$C_{30}$ alkenyl radical which can carry one or more hydroxyl substituents and which can comprise, in the carbonaceous chain, one or more heteroatoms chosen from oxygen, nitrogen and silicon atoms.

Although only the isomers in which the cyano substituent is in the cis position with respect to the para-aminophenyl substituent are represented in the above formula (13), this formula should be understood as also encompassing the corresponding trans isomers; for each of the two double bonds, and independently, the cyano and para-aminophenyl substituents can be in the cis or trans configuration with respect to one another.

Mention may be made, as example, of the dimer of 2-ethylhexyl 2-cyano-3-[4-(acetylamino)phenyl]-acrylate of formula:

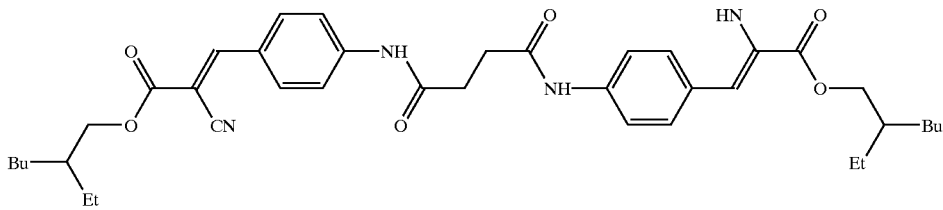

Another specific family of insoluble organic screening agents in accordance with the invention are the polyvalent metal salts (for example, $Ca^{2+}$, $Zn^{2+}$, $Mg^{2+}$, $Ba^{2+}$, $Al^{3+}$ or $Zr^{4+}$) of sulfonic or carboxylic organic screening agents, such as the polyvalent metal salts of sulfonated derivatives of benzylidenecamphor, such as those disclosed in Application FR-A 2 639 347; the polyvalent metal salts of sulfonated derivatives of benzimidazole, such as those disclosed in Application EP-A-893 119; or the polyvalent metal salts of cinnamic acid derivatives, such as those disclosed in Application JP-87 166 517.

Mention may also be made of metal or ammonium or substituted ammonium complexes of UV-A and/or UV-B organic screening agents as disclosed in Patent Applications WO 93/10753, WO 93/11095 and WO 95/05150.

The insoluble UV screening agent or agents of the invention are present at a total concentration preferably ranging from 1 to 10% by weight approximately and more particularly from 2 to 8% by weight with respect to the total weight of the composition.

The amino-substituted 2-hydroxybenzophenone derivatives in accordance with the invention correspond to the following formula (I):

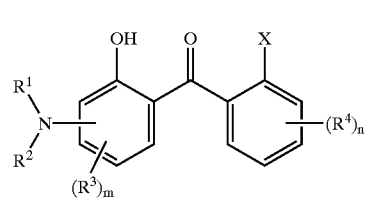

in which:

$R^1$ and $R^2$, which are identical or different, denote a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical;

$R^1$ and $R^2$ can also form, with the nitrogen atom with which they are bonded, a 5- or 6-membered heterocyclic ring member;

$R^3$ and $R^4$, which are identical or different, denote a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$ alkoxycarbonyl radical, a $C_1$–$C_{12}$ alkylamino radical, a di($C_1$–$C_{12}$)alkylamino radical, an aryl radical or a heteroaryl which is optionally substituted, or a water-solubilizing substituent chosen from a carboxylate group, a sulfonate group or an ammonium residue;

X denotes a hydrogen atom or a $COOR^5$ or $CONR^6R^7$ group;

$R^5$, $R^6$ and $R^7$, which are identical or different, denote a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(YO)$_o$—Z group or an aryl group;

Y denotes —(CH$_2$)$_2$—, —(CH$_2$)$_3$—, —(CH$_2$)$_4$— or —CH—(CH$_3$)—CH$_2$—; Z represents —CH$_2$—CH$_3$, —CH$_2$CH$_2$CH$_3$, —CH$_2$—CH$_2$—CH$_2$—CH$_3$ or —CH(CH$_3$)—CH$_3$;

m is an integer varying from 0 to 3;

n is an integer varying from 0 to 3;

o is an integer varying from 1 to 2.

Mention may be made, as $C_1$–$C_{20}$ alkyl radicals, of, for example: methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

Mention may be made, as C$_2$–C$_{10}$ alkenyl groups, of, for example: vinyl, n-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Mention may be made, as C$_1$–C$_{12}$ alkoxy radicals, of: methoxy, ethoxy, n-propoxy, n-butoxy, n-pentoxy, 1-methylpropoxy, 3-methylbutoxy, 2,2-dimethylpropoxy, 1-methyl-1-ethylpropoxy, octoxy, 2-methylpropoxy, 1,1-dimethylpropoxy, hexoxy, heptoxy or 2-ethylhexoxy.

Mention may be made, as C$_3$–C$_{10}$ cycloalkyl radicals, of, for example: cyclopropyl, cyclobutyl, cyclopentyl, cyclohexyl, cycloheptyl, 1-methylcyclo-propyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Mention may be made, as C$_3$–C$_{10}$ cycloalkenyl radicals having one or more double bonds, of: cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl. The cycloalkyl or cycloalkenyl radicals can comprise one or more substituents (preferably from 1 to 3) chosen, for example, from halogen, such as chlorine, fluorine or bromine; cyano; nitro; amino; C$_1$–C$_4$ alkylamino; di(C$_1$–C$_4$)alkylamino; C$_1$–C$_4$ alkyl; C$_1$–C$_4$ alkoxy; or hydroxyl. They can also comprise from 1 to 3 heteroatoms, such as sulfur, oxygen or nitrogen, the free valencies of which can be occupied by a hydrogen or a C$_1$–C$_4$ alkyl radical.

The aryl groups are preferably chosen from phenyl or naphthyl rings which can comprise one or more substituents (preferably from 1 to 3) chosen, for example, from halogen, such as chlorine, fluorine or bromine; cyano; nitro; amino; C$_1$–C$_4$ alkylamino; di(C$_1$–C$_4$)alkylamino; C$_1$–C$_4$ alkyl; C$_1$–C$_4$ alkoxy; or hydroxyl. Preference is more particularly given to phenyl, methoxyphenyl and naphthyl.

The heteroaryl groups generally comprise one or more heteroatoms chosen from sulfur, oxygen or nitrogen.

The water-solublizing groups are, for example, carboxylate or sulfonate groups and more particularly their salts with physiologically acceptable cations, such as alkali metal salts or trialkylammonium salts, such as tri(hydroxyalkyl)-ammonium or 2-methylpropan-1-ol-2-ammonium salts. Mention may also be made of ammonium groups, such as alkylammoniums, and their salified forms with physiologically acceptable anions.

Mention may in particular be made, as examples of the 5- or 6-membered heterocyclic ring member formed by the R$^1$ and R$^2$ radicals with the nitrogen atom, of pyrrolidine or piperidine.

The amino groups can be attached to the benzene ring in the ortho, meta or para position with respect to the carbonyl radical and more preferably in the para position.

A family of preferred compounds of formula (I) comprises those chosen from those of following formula (Ia):

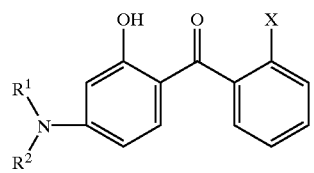

(Ia)

in which:
R$^1$ and R$^2$, which are identical or different, denote a hydrogen atom or a C$_1$–C$_{12}$ alkyl radical or form, with the nitrogen atom with which they are bonded, a 5- or 6-membered heterocyclic ring member;
X denotes COOR$^5$ or CONR$^6$R$^7$;
R$^5$ denotes a hydrogen atom, a C$_1$–C$_{12}$ alkyl radical or a C$_3$–C$_6$ cycloalkyl radical;
R$^6$ and R$^7$, which are identical or different, denote a hydrogen atom, a C$_1$–C$_{12}$ alkyl radical or a C$_5$–C$_6$ cycloalkyl radical.

The more particularly preferred compounds of formula (Ia) are those for which:
R$^1$ and R$^2$, which are identical or different, denote a C$_1$–C$_4$ alkyl radical and more particularly ethyl;
R$^5$ denotes a C$_3$–C$_8$ alkyl radical;
R$^6$ and R$^7$, which are identical or different, denote a C$_1$–C$_8$ alkyl radical.

Another family of preferred compounds of formula (I) comprises those chosen from those of following formula (Ib):

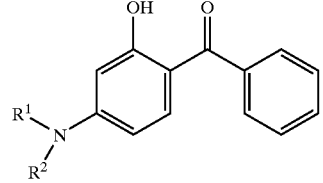

(Ib)

in which:
R$^1$ and R$^2$, which are identical or different, denote a C$_1$–C$_{12}$ alkyl radical or form, with the nitrogen atom with which they are bonded, a 5- or 6-membered heterocyclic ring member.

Mention may more particularly be made, among the compounds of formula (Ib), of:
4-diethylamino-2-hydroxyphenyl phenyl ketone,
4-pyrrolidino-2-hydroxyphenyl phenyl ketone.

A family of more particularly preferred compounds of formula (I) comprises those chosen from those of following formula (Ic):

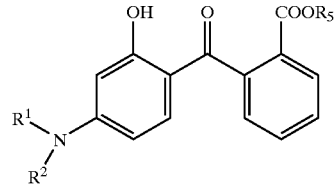

(Ic)

in which:
R$^1$ and R$^2$, which are identical or different, denote a hydrogen atom or a C$_1$–C$_8$ alkyl radical or form, with the nitrogen atom with which they are bonded, a 5- or 6-5 membered ring;

$R^5$ denotes a hydrogen atom, a $C_1$–$C_{12}$ alkyl radical or a $C_3$–$C_6$ cycloalkyl radical.

Mention may be made, among the compounds of formula (Ic), of:

2-(4-pyrrolidino-2-hydroxybenzoyl)benzoate methyl 2-(4-diethylamino-2-hydroxybenzoyl)benzoate 2-ethylhexyl 2-(4-diethylamino-2-hydroxybenzoyl)-benzoate cyclohexyl 2-(4-diethylamino-2-hydroxybenzoyl)-benzoate n-hexyl 2-(4-diethylamino-2-hydroxybenzoyl)benzoate

[lacuna] 2-(4-dibutylamino-2-hydroxybenzoyl)benzoate methyl 2-(4-dibutylamino-2-hydroxybenzoyl)benzoate isobutyl 2-(4-dibutylamino-2-hydroxybenzoyl)benzoate.

A very particularly preferred compound of formula (I) is n-hexyl 2-(4-diethylamino-2-hydroxy-benzoyl)benzoate.

The compounds of formula (I) as defined above are known per se and their structures and their syntheses are disclosed in Patent Applications EP-A-1 046 391 and DE 100 12 408 (which form an integral part of the content of the description).

The amino-substituted 2-hydroxybenzophenone derivatives in accordance with the invention are preferably present in the composition of the invention in proportions preferably ranging from 0.1 to 20% by weight and more preferably from 0.1 to 15% by weight and more particularly from 0.5 to 10% by weight with respect to the total weight of the composition.

In addition, the compositions in accordance with the invention can comprise other additional, water-soluble or fat-soluble, organic UV screening agents which are active in the UV-A and/or UV-B regions (absorbers).

The additional organic UV screening agents are chosen in particular from anthranilates; cinnamic derivatives; salicylic derivatives; camphor derivatives, other than the compound (II); triazine derivatives, such as those disclosed in U.S. Pat. No. 4,367,390, EP 863 145, EP 517 104, EP 570 838, EP 796 851, EP 775 698, EP 878 469 and EP 933 376; benzophenone derivatives, other than those of formula (I); β,β-diphenylacrylate derivatives; benzotriazole derivatives; benzalmalonate derivatives; benzimidazble derivatives; imidazolines; bisbenzoazolyl derivatives as disclosed in Patents EP 669 323 and U.S. Pat. No. 2,463,264; p-aminobenzoic acid (PABA) derivatives; methylenebis (hydroxyphenylbenzotriazole)derivatives as disclosed in U.S. Pat. Nos. 5,237,071, 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; and 4,4-diarylbutadienes as disclosed in Applications EP 0 967 200, DE 197 46 654, DE 197 55 649 and EP-A-1 008 586.

Mention may be made, as examples of additional organic screening agents which are active in the UV-A and/or UV-B regions, of, denoted below under their INCI names:

para-Aminobenzoic Acid Derivatives:

PABA,

Ethyl PABA,

Ethyl Dihydroxypropyl PABA,

Ethylhexyl Dimethyl PABA, sold in particular under the name "Escalol 507" by ISP, Glyceryl PABA, PEG-PABA, sold under the name "Uvinul P25" by BASF, Salicylic Derivatives:

Homosalate, sold under the name "Eusolex HMS" by Rona/EM Industries,

Ethylhexyl Salicylate, sold under the name "Neo Heliopan OS" by Haarmann and Reimer, Dipropyleneglycol Salicylate, sold under the name "Dipsal" by Scher, TEA Salicylate, sold under the name "Neo Heliopan TS" by Haarmann and Reimer, Dibenzoylmethane Derivatives:

Butyl Methoxydibenzoylmethane, sold in particular under the trade name "Parsol 1789" by Hoffmann-LaRoche, Isopropyl Dibenzoylmethane, Cinnamic Derivatives:

Ethylhexyl Methoxycinnamate, sold in particular under the trade name "Parsol MCX" by Hoffmann-LaRoche, Isopropyl Methoxy cinnamate, Isoamyl Methoxy cinnamate, sold under the trade name "Neo Heliopan E 1000" by Haarmann and Reimer, Cinoxate, DEA Methoxycinnamate, Diisopropyl Methylcinnamate, Glyceryl Ethylhexanoate Dimethoxycinnamate, β,β-Diphenylacrylate Derivatives:

Octocrylene, sold in particular under the trademark "Uvinul N539" by BASF,

Etocrylene, sold in particular under the trade name "Uvinul N35" by BASF,

Benzophenone Derivatives:

Benzophenone-1, sold under the trade name "Uvinul 400" by BASF,

Benzophenone-2, sold under the trade name "Uvinul D50" by BASF,

Benzophenone-3 or Oxybenzone, sold under the trade name "Uvinul M40" by BASF,

Benzophenone-4, sold under the trade name "Uvinul MS40" by BASF,

Benzophenone-5,

Benzophenone-6, sold under the trade name 15 "Helisorb 11" by Norquay,

Benzophenone-8, sold under the trade name "SpectraSorb UV-24" by American Cyanamid, Benzophenone-9, sold under the trade name "Uvinul DS-49" by BASF, Benzophenone-12, Benzylidenecamphor Derivatives:

3-Benzylidene camphor, manufactured under the name "Mexoryl SD" by Chimex,

4-Methylbenzylidene camphor, sold under the name "Eusolex 6300" by Merck,

Benzylidene Camphor Sulfonic Acid, manufactured under the name "Mexoryl SL" by Chimex, Camphor Benzalkonium Methosulfate, manufactured under the name "Mexoryl SO" by Chimex, Polyacrylamidomethyl Benzylidene Camphor, manufactured under the name "Mexoryl SW" by 5 Chimex, Phenylbenzimidazole Derivatives:

Phenylbenzimidazole Sulfonic Acid, sold in particular under the trade name "Eusolex 232" by Merck, Disodium Phenyl Dibenzimidazole Tetrasulfonate, sold under the trade name "Neo Heliopan AP" by Haarmann and Reimer, Triazine Derivatives:

Anisotriazine, sold under the trade name "Tinosorb S" by Ciba Specialty Chemicals, Ethylhexyl triazone, sold in particular under the trade name "Uvinul T150" by BASF, Diethylhexyl Butamido Triazone, sold under the trade name "Uvasorb HEB" by Sigma 3V, 2,4,6-tris(diisobutyl 4'-aminobenzalmalonate)-s-triazine, Phenylbenzotriazole Derivatives:

Drometrizole Trisiloxane, sold under the name "Silatrizole" by Rhodia Chimie,

Methylenebis(benzotriazolyltetramethylbutyl-phenol), sold in the solid form under the trade name "Mixxim BB/100" by Fairmount Chemical or in the micronized form in aqueous dispersion under the trade name "Tinosorb M" by Ciba Specialty Chemicals, Anthranilic Derivatives:

Menthyl anthranilate, sold under the trade name "Neo Heliopan MA" by Haarmann and Reimer, Imidazoline Derivatives:

Ethylhexyl Dimethoxybenzylidene Dioxoimidazoline Propionate,

Benzalmalonate Derivatives:

Polyorganosiloxane comprising a benzalmalonate functional group, sold under the trade name "Parsol SLX" by Hoffmann-LaRoche, 4,4-Diarylbutadiene Derivatives:

1,1-dicarboxy (2,2'-diméthyl-propyl)-4,4-diphénylbutadiène and their mixtures.

The soluble organic UV screening agents which are more particularly preferred are chosen from the following compounds:

Ethylhexyl Salicylate,

Octocrylene,

Ethylhexyl Methoxycinnamate,

Butyl Methoxydibenzoylmethane,

Phenylbenzimidazole Sulfonic Acid,

Benzophenone-3,

Benzophenone-4,

Benzophenone-5,

4-Methylbenzylidene camphor,

Disodium Phenyl Dibenzimidazole Tetrasulfonate,

Anisotriazine,

Ethylhexyl triazone,

Diethylhexyl Butamido Triazone, 2,4, 6-Tris(diisobutyl 4' -aminobenzalmalonate)-s-triazine, Drometrizole Trisiloxane, Methylenebis(benzotriazolylietramethylbutyl-phenol), 1,1-dicarboxy (2,2'-diméthyl-propyl)-4,4-diphénylbutadiène, and their mixtures.

The cosmetic compositions according to the invention can also comprise pigments or alternatively nanopigments (mean size of the primary particles: generally between 5 nm and 100 nm, preferably between 10 nm and 50 nm) formed from coated or uncoated metal oxides, such as, for example, nanopigments formed from titanium oxide (amorphous or crystallized in the rutile and/or anatase form), iron oxide, zinc oxide, zirconium oxide or cerium oxide, which are all UV photoprotective agents well known per se. Conventional coating agents are, furthermore, alumina and/or aluminium stearate. Such coated or uncoated metal oxide nanopigments are disclosed in particular in Patent Applications EP-A-0 518 772 and EP-A-0 518 773.

The compositions according to the invention can also comprise agents for the artificial tanning and/or browning of the skin (self-tanning agents), such as, for example, dihydroxyacetone (DHA).

The compositions of the invention can additionally comprise conventional cosmetic adjuvants chosen in particular from fatty substances, organic solvents, ionic or nonionic thickeners, softeners, antioxidants, agents for combating free radicals, opacifiers, stabilizers, emollients, silicones, $\alpha$-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, colorants or any other ingredient commonly used in cosmetics, in particular for the manufacture of antisun compositions in the form of emulsions.

The fatty substances can be composed of an oil or a wax or their mixtures. The term "oil" is understood to mean a compound which is liquid at ambient temperature. The term "wax" is understood to mean a compound which is solid or substantially solid at ambient temperature and for which the melting point is generally greater than 35° C. They also comprise fatty acids, fatty alcohols and esters of fatty acids which are linear or cyclic, such as derivatives of benzoic acid, trimellitic acid and hydroxybenzoic acid.

Mention may be made, as oils, of mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$–$C_{15}$ alkyl benzoate sold under the trade name "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; or polyalkylenes.

Mention may be made, as waxy compounds, of paraffin wax, carnauba wax, beeswax or hydrogenated castor oil.

Mention may be made, among organic solvents, of lower alcohols and polyols.

Of course, a person skilled in the art will take care to choose this or these optional additional compounds and/or their amounts so that the advantageous properties, in particular the synergistic effect, intrinsically attached to the compositions in accordance with the invention are not, or not substantially, detrimentally affected by the envisaged addition or additions.

The compositions of the invention can be prepared according to techniques well known to a person skilled in the art, in particular those intended for the preparation of emulsions of oil-in-water or water-in-oil type.

These compositions can be provided in particular in the form of a simple or complex emulsion (O/W, W/O, O/W/O or W/O/W), such as a cream, a milk, a gel or a cream gel, of a powder or of a solid tube and can optionally be packaged as an aerosol and provided in the form of a foam or spray.

When it is a question of an emulsion, the aqueous phase of the latter can comprise a nonionic vesicular dispersion prepared according to known processes (Bangham, Standish and Watkins, J. Mol. Biol., 13, 238 (1965), FR 2 315 991 and FR 2 416 008).

The cosmetic composition of the invention can be used as a composition for protecting the human epidermis or the hair against ultraviolet rays, as an antisun composition or as a make-up product.

When the cosmetic composition according to the invention is used for the protection of the human epidermis against UV rays or as an antisun composition, it can be provided in the form of a suspension or dispersion in solvents or fatty substances, in the form of a nonionic vesicular dispersion or in the form of an emulsion, preferably of oil-in-water type, such as a cream or a milk, in the form of an ointment, gel, cream gel, solid tube, powder, stick, aerosol foam or spray.

When the cosmetic composition according to the invention is used for the protection of the hair against UV rays, it can be provided in the form of a shampoo, lotion, gel, emulsion or nonionic vesicular dispersion and can constitute, for example, a rinse-out composition, to be applied before or after shampooing, before or after dyeing or bleaching, and before, during or after perming or hair straightening, a styling or treating lotion or a styling or treating gel, a lotion or a gel for blow-drying or hair setting, or a composition for perming or straightening, dyeing or bleaching the hair.

When the composition is used as a product for making up the eyelashes, eyebrows or skin, such as a treatment cream for the epidermis, foundation, lipstick tube, eyeshadow, face powder, mascara or eyeliner, it can be provided in the anhydrous or aqueous, pasty or solid form, such as oil-in-water or water-in-oil emulsions, nonionic vesicular dispersions, or suspensions.

By way of indication, for the antisun formulations in accordance with the invention which exhibit a vehicle of oil-in-water emulsion type, the aqueous phase (comprising in particular the hydrophilic screening agents) generally represents from 50 to 95% by weight, preferably from 70 to 90% by weight, with respect to the entire formulation, the oily phase (comprising in particular the lipophilic screening agents) from 5 to 50% by weight, preferably from 10 to 30% by weight, with respect to the entire formulation, and the (co)emulsifier(s) from 0.5 to 20% by weight, preferably from 2 to 10% by weight, with respect to the entire formulation.

Concrete but in no way limiting examples illustrating the invention will now be given.

EXAMPLE 1

The following specific composition according to the present invention was formulated via simple intimate admixing of the several constituents thereof:

| | |
|---|---|
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| $C_{12}$–$C_{15}$ Alkyl benzoate (Witconol TN, Witco) | 10 g |
| n-Hexyl 2-(4-diethylamino-2-hydroxybenzoyl)-benzoate | 2 g |
| Glycerol | 10 g |
| Methylenebis(benzotriazolyltetramethyl-butylphenol) (Tinosorb M, Ciba) | 10 g |
| Preservatives | q.s. |
| Demineralized water | q.s. for 100 g |

EXAMPLE 2

The following specific composition according to the present invention was formulated via simple intimate admixing of the several constituents thereof:

| | | |
|---|---|---|
| Glycerol mono/distearate/polyethylene glycol (100 EO) stearate mixture (Arlacel 165 FL, ICI) | | 2 g |
| Stearyl alcohol (Lanette 18, Henkel) | | 1 g |
| Palm oil stearic acid (Stéarine TP, Stéarinerie Dubois) | | 2.5 g |
| Polydimethylsiloxane (Dow Corning 200 Fluid, Dow Corning) | | 0.5 g |
| $C_{12}$/$C_{15}$ Alkyl benzoate (Witconol TN, Witco) | | 15 g |
| Triethanolamine | | 0.5 g |
| n-Hexyl 2-(4-diethylamino-2-hydroxybenzoyl)-benzoate | | 2.5 g |
| Glycerol | | 5 g |
| Hexadecyl phosphate, potassium salt (Amphisol K, Hoffmann-LaRoche) | | 1 g |
| Polyacrylic acid (Synthalen K, 3V) | | 0.3 g |
| Hydroxypropyl methyl cellulose (Methocel F4M, Dow Chemical) | | 0.1 g |
| 2,2'-(1,4-Phenylene)bisbenzoxazole | | 4 g |
| Triethanolamine | q.s. | pH 7 |
| Preservatives | q.s. | |
| Demineralized water | q.s. for | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological sunscreen composition suited for the UV-photoprotection of human skin and/or hair, comprising synergistically UV-$A_{PPD}$-enhancing amounts of (a) particulates of at least one insoluble organic UV-screening agent having a particle size ranging from 10 nm to 5 μm, and (b) at least one UV-screening amino-substituted 2-hydroxybenzophenone compound having the following structural formula (I):

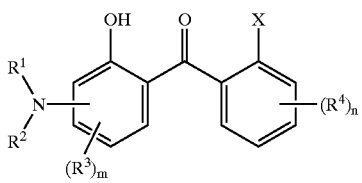

(I)

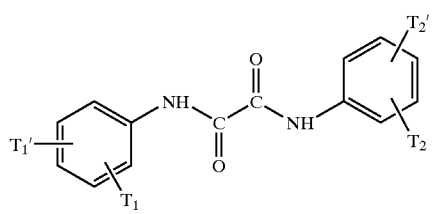

(1)

in which R¹ and R², which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that R¹ and R² can together form, with the nitrogen atom to which they are bonded, a 5- or 6-membered heterocyclic ring member; R³ and R⁴, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$ alkoxycarbonyl radical, a $C_1$–$C_{12}$ alkylamino radical, a di($C_1$–$C_{12}$) alkylamino radical, an aryl radical or a heteroaryl radical which is optionally substituted, or a water-solubilizing substituent selected from among a carboxylate group, a sulfonate group or an ammonium residue; X is a hydrogen atom or a —COOR⁵ or —CONR⁶R⁷ radical; R⁵, R⁶ and R⁷, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(YO)$_o$—Z radical or an aryl radical; Y is —(CH$_2$)$_2$—, —(CH$_2$)$_3$—, —(CH$_2$)$_4$— or —CH—CH$_3$—CH$_2$—; Z is —CH$_2$—CH$_3$, —CH$_2$CH$_2$CH$_3$, —CH$_2$—CH$_2$-CH$_3$ or —CH(CH$_3$)—CH$_3$; m is an integer ranging from 0 to 3; n is an integer ranging from 0 to 3; o is an integer ranging from 1 to 2, formulated into (c) a topically applicable, cosmetically/dermatologically acceptable vehicle, diluent or carrier therefor.

2. The cosmetic/dermatological sunscreen composition as defined by claim 1, said at least one UV-screening agents (a) and (b) being present in a proportion eliciting synergistic activity with regard to the sun protection factors UV-A$_{PPD}$ conferred.

3. The cosmetic/dermatological sunscreen composition as defined by claim 1, said at least one insoluble organic UV-screening agent comprising an oxalanilide compound, a triazine compound, a benzotriazole compound, a vinyl amide compound, a cinnamamide compound, a compound which comprises one or more benzazole and/or benzofuran or benzothiophene groups, an indole compound, an aryl vinylene ketone compound, a phenylenebis(benzoxazinone) compound, or an acrylonitrile amide, sulfonamide or carbamate compound.

4. The cosmetic/dermatological sunscreen composition as defined by claim 3, comprising at least one oxalanilide UV-screening agent having the formula (1):

in which $T_1$, $T'_1$, $T_2$ and $T'_2$, which may be identical or different, are each a hydrogen atom, a $C_1$–$C_8$ alkyl radical or a $C_1$–$C_8$ alkoxy radical.

5. The cosmetic/dermatological sunscreen composition as defined by claim 4, said at least one oxalanilide UV-screening agent having one of the formulae:

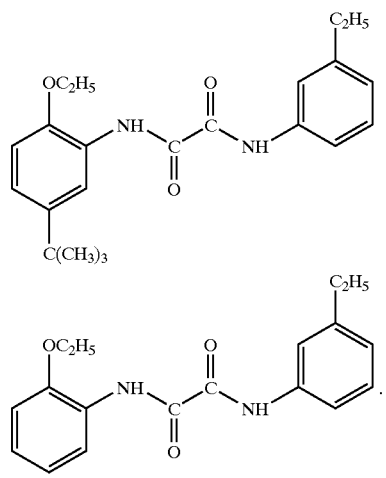

6. The cosmetic/dermatological sunscreen composition as defined by claim 3, said at least one insoluble UV-screening agent comprising a triazine compound having the formula:

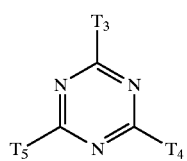

(2)

in which $T_3$, $T_4$ and $T_5$ are independently phenyl, phenoxy or pyrrolo, in which the phenyl, phenoxy and pyrrolo groups are optionally substituted by one, two or three substituents selected from among OH, $C_1$–$C_{18}$ alkyl or alkoxy, $C_1$–$C_{18}$ carboxyalkyl, $C_5$–$C_8$ cycloalkyl, a methylbenzylidenecamphor radical, a —(CH=CH)$_n$(CO)—OT$_6$ radical, with $T_6$ either $C_1$–$C_{18}$ alkyl or cinnamyl, and n is the value 0 or 1.

7. The cosmetic/dermatological sunscreen composition as defined by claim 3, said at least one UV-screening agent comprising a triazine compound selected from among insoluble s-triazine compounds substituted by benzalmalonate and/or phenylcyanoacrylate groups.

8. The cosmetic/dermatological sunscreen composition as defined by claim 7, said at least one UV-screening agent comprising a triazine compound being selected from among 2,4,6-tris(diethyl 4'-aminobenzalmalonate)-s-triazine, 2,4,6-tris(diisopropyl 4'-aminobenzalmalonate)-s-triazine, 2,4,6- tris(dimethyl 4'-aminobenzalmalonate)-s-triazineand/or 2,4,6-tris(ethyl α-cyano-4-aminocinnamate)-s-triazine.

9. The cosmetic/dermatological sunscreen composition as defined by claim 3, said at least one UV-screening agent comprising a triazine compound being selected from among insoluble s-triazine compounds substituted by benzotriazole and/or benzothiazole groups.

10. The cosmetic/dermatological sunscreen composition as defined by claim 9, said at least one UV-screening agent comprising a triazine compound selected from among 2,4,6-tris[(3'-(benzotriazol-2-yl)-2'-hydroxy-5'-methyl)phenylamino]-s-triazine and/or 2,4,6-tris[(3'-(benzotriazol-2-yl)-2'-hydroxy-5'-tert-octyl)phenylamino]-s-triazine.

11. The cosmetic/dermatological sunscreen composition as defined by claim 3, said at least one organic UV-screening agent comprising a benzotriazole compound having the following formula (3):

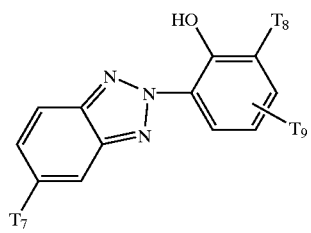

(3)

in which $T_7$ is a hydrogen atom or a $C_1$–$C_{18}$ alkyl radical; and $T_8$ and $T_9$, which may be identical or different, are each a $C_1$–$C_{18}$ alkyl radical optionally substituted by a phenyl radical.

12. The cosmetic/dermatological sunscreen composition as defined by claim 11, said compound of formula (3) having one of the following formulae:

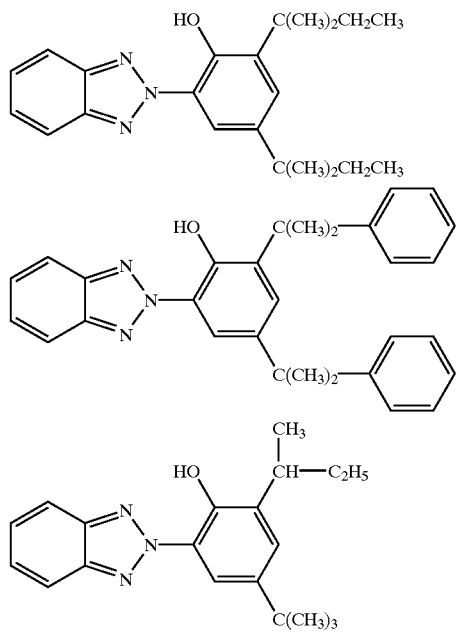

-continued

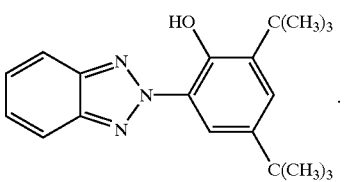

13. The cosmetic/dermatological sunscreen composition as defined by claim 3, said at least one insoluble UV-screening agent comprising [2,4'-dihydroxy-5 3-(2H-benzotriazol-2-yl)-5-(1,1,3,3-tetramethylbutyl)-2'-(n-octoxy)-5-benzoyl]diphenylmethane having the structural formula:

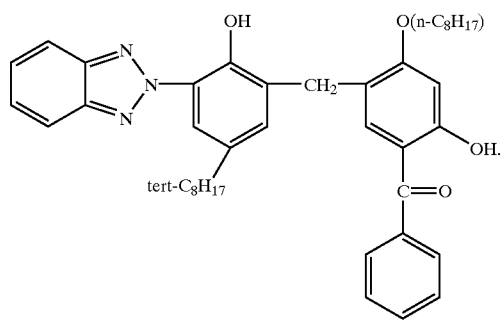

14. The cosmetic/dermatological sunscreen composition as defined by claim 3, said at least one organic UV-screening agent comprising a benzotriazole compound selected from among methylenebis(hydroxyphenylbenzo-triazole) compounds having the following structural formula:

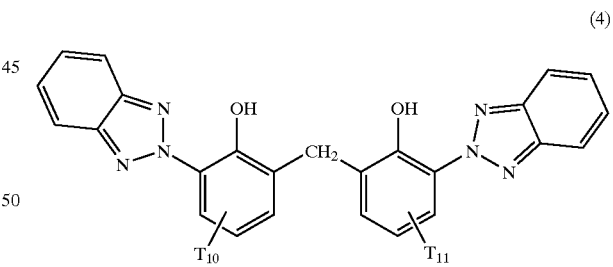

(4)

in which the $T_{10}$ and $T_{11}$ radicals, which maybe identical or different, are each a $C_1$–$C_{18}$ alkyl radical which can be substituted by one or more radicals selected from among a $C_1$–$C_4$ alkyl radical, a $C_5$–$C_{12}$ cycloalkyl radical or an aryl residue.

15. The cosmetic/dermatological sunscreen composition as defined by claim 14, said at least one compound of formula (4) being selected from among those having the structural formulae:

compound (a)

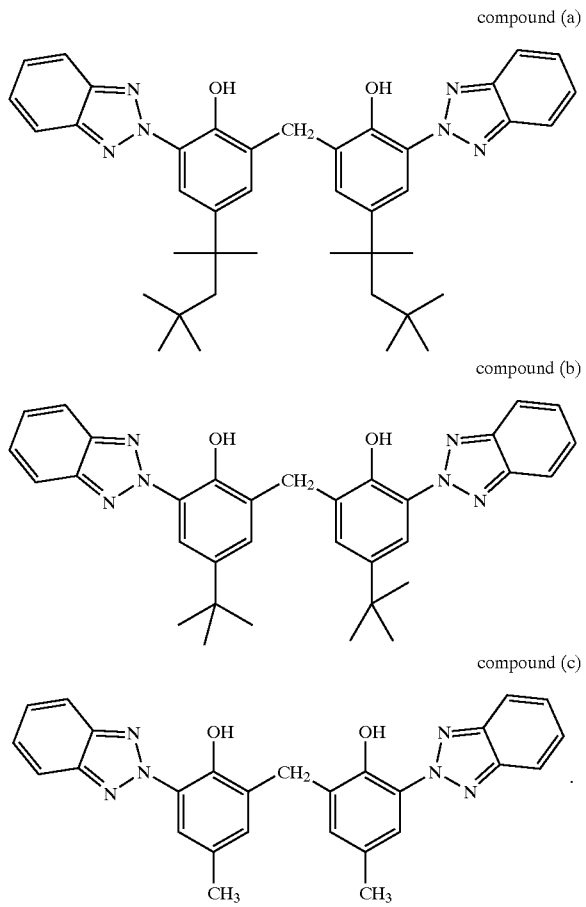

compound (b)

compound (c)

16. The cosmetic/dermatological sunscreen composition as defined by claim 3, said at least one organic UV-screening agent comprising a vinyl amide compound having the following formula:

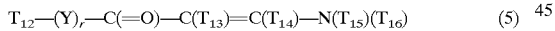

$$T_{12}-(Y)_r-C(=O)-C(T_{13})=C(T_{14})-N(T_{15})(T_{16}) \quad (5)$$

in which $T_{12}$ is a $C_1$–$C_{18}$ alkyl radical, or a phenyl radical optionally substituted by one, two or three radicals selected from among OH, a $C_1$–$C_{18}$ alkyl radical, a $C_1$–$C_8$ alkoxy radical, or a group —C(=O)—OT$_{17}$ wherein $T_{17}$ is a $C_1$–$C_{18}$ alkyl; $T_{13}$, $T_{14}$, $T_{15}$ and $T_{16}$, which may be identical or different, are each a $C_1$–$C_{18}$ alkyl radical or a hydrogen atom; Y is N or O; and r is 0 or 1.

17. The cosmetic/dermatological sunscreen composition as defined by claim 16, said compounds of formula (5) comprising 4-octylamino-3-penten-2-one; ethyl 3-octylamino-3-butenoate; 3-octylamino-1-phenyl-2-buten-1-one; and/or 3-dodecylamino-1-phenyl-2-buten-1-one.

18. The cosmetic/dermatological sunscreen composition as defined by claim 3, said at least one organic UV-screening agent comprising a cinnamamide compound having the following formula:

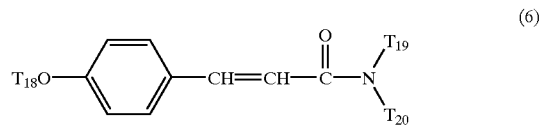

in which OT$_{18}$ is a hydroxyl or $C_1$–$C_4$ alkoxy radical; $T_{19}$ is hydrogen or $C_1$–$C_4$ alkyl; $T_{20}$ is a —(CONH)$_s$-phenyl radical wherein s is 0 or 1 and the phenyl radical can be substituted by one, two or three groups selected from among OH, $C_1$–$C_{18}$ alkyl, $C_1$–$C_8$ alkoxy, or a —C(=O)—OT$_{21}$ group wherein $T_{21}$ is a $C_1$–$C_{18}$ alkyl radical.

19. The cosmetic/dermatological sunscreen composition as defined by claim 3, said at least one insoluble UV-screening agent comprising a cinnamamide dimer.

20. The cosmetic/dermatological sunscreen composition as defined by claim 19, said at least one insoluble UV-screening agent comprising a compound having the structural formula:

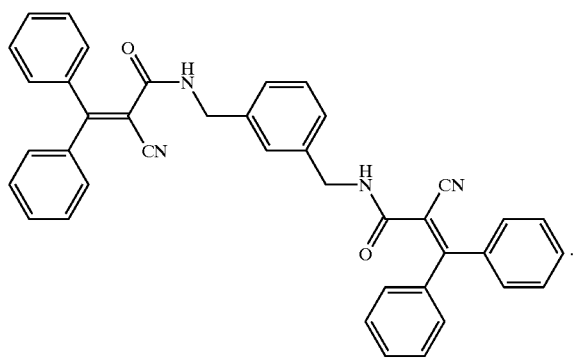

21. The cosmetic/dermatological sunscreen composition as defined by claim 3, said at least one insoluble UV-screening agent comprising a benzazole compound selected from among those of the following formulae (7), (8) and (9):

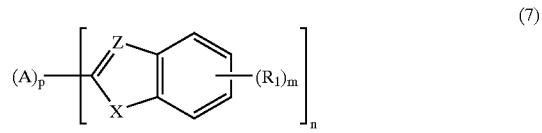

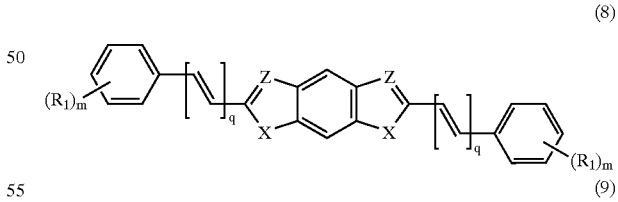

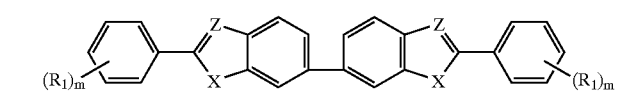

in which each of the X symbols independently is an oxygen or sulfur atom, or an NR$_2$ group; each of the Z symbols independently is a nitrogen atom or a CH group; each of the R$_1$ symbols independently is an OH group, a halogen atom, a linear or branched $C_{1-8}$ alkyl group; optionally comprising a silicon atom, or a linear or branched $C_{1-8}$ alkoxy group; each of the numbers m independently is 0, 1 or 2; n is an integer ranging from 1 to 4, inclusive; p is equal to 0 or 1; each of the numbers q is independently equal to 0 or 1; each of the R$_2$ symbols independently is a hydrogen atom or a benzyl or linear or branched C$_{1-8}$ alkyl radical, optionally comprising a silicon atom; A is a radical with a valency n selected from among of the formulae:

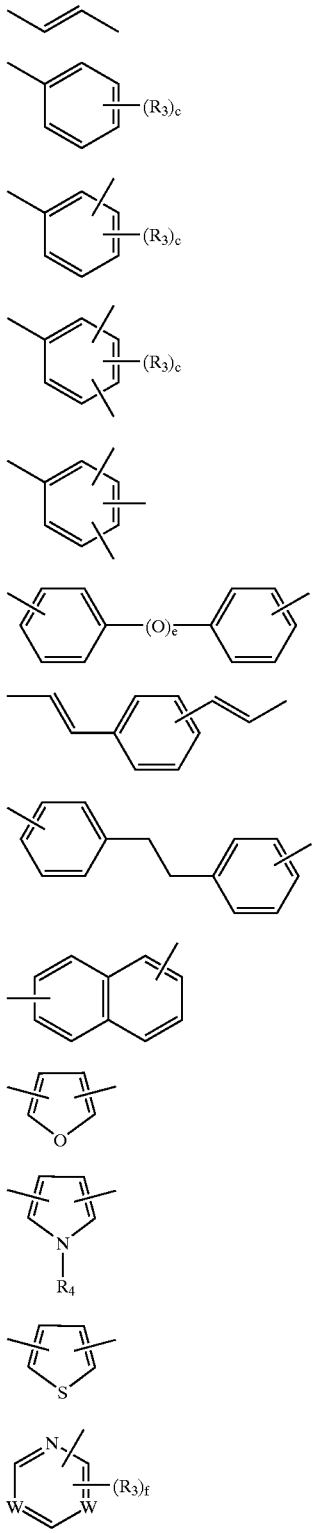

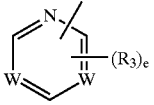

(n)

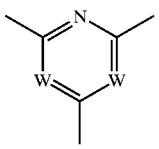

(o)

in which W is N or CH; each of the R$_3$ symbols independently is a halogen atom, or a linear or branched C$_{1-4}$ alkyl or alkoxy radical, or a hydroxyl group; R$_4$ is a hydrogen atom or a linear or branched C$_{1-4}$ alkyl radical; c=0–4, d=0–3, e=0 or 1 and f=0–2.

22. The cosmetic/dermatological sunscreen composition as defined by claim 21, comprising a benzazole compound of formula (7) selected from among 2-(benzoxazol-2-yl)-4-methylphenol, 2-(1H-benzimidazol-2-yl)-4-methoxyphenol or 2-(benzothiazol-2-yl)phenol, 2,2'-bisbenzimidazole, 5,5', 6,6'-tetramethyl-2,2'-bis-benzimidazole, 5,5'-dimethyl-2,2'-bisbenzimidazole, 6-methoxy-2,2'-bisbenzimidazole, 2-(1H-benzimidazol-2-yl)benzothiazole, 2-(1H-benzimidazol-2-yl)benzoxazole and N,N'-dimethyl-2,2'-bisbenzimidazole, 1,4-phenylene-bis(2-benzoxazolyl), 1,4-phenylenebis(2-benzimi-dazolyl), 1,3-phenylenebis(2-benzoxazolyl), 1,2-phenylenebis(2-benzoxazolyl), 1,2-phenylenebis-(benzimidazolyl), 1,4-phenylenebis(N-(2-ethylhexyl)-2-benzimidazolyl) and 1,4-phenylenebis(N-trimethyl-silylmethyl-2-benzimidazolyl), 2-(2-benzofuranyl)-benzoxazole, 2-(benzofuranyl)-5-methylbenzoxazole and/or 2-(3-methyl-2-benzofuranyl) benzoxazole.

23. The cosmetic/dermatological sunscreen composition as defined by claim 21, comprising a benzazole compound of formula (8) selected from among 2,6-diphenyl-1,7-dihydrobenzo[1,2-d;4,5-d']diimidazole, 2,6-distyryl-1,7-dihydrobenzo[1,2-d;4,5-d']diimidazole and/or 2,6-di(p-tert-butylstyryl)-1,7-dihydrobenzo[1,2-d;4,5-d']diimidazole.

24. The cosmetic/dermatological sunscreen composition as defined by claim 21, comprising a benzazole compound of formula (9) that is 5,5'-bis(2-phenylbenzimidazole).

25. The cosmetic/dermatological sunscreen composition as defined by claim 21, said at least one insoluble UV-screening agent comprising a benzazole compound selected from among 2-(1H-benzimidazol-2-yl) benzoxazole, 6-methoxy-2,2'-bisbenzimidazole, 2-(1H-benzimidazol-2-yl)benzothiazole, 1,4-phenylenebis(2-benzoxazolyl), 1,4-phenylenebis(2-benzimidazolyl), 1,3-phenylene-bis(2-benzoxazolyl), 1,2-phenylenebis(2-benzoxazolyl), 1,2-phenylenebis(2-benzimidazolyl) and/or 1,4-phenylene-bis(N-trimethylsilylmethyl-2-benzimidazolyl).

26. The cosmetic/dermatological sunscreen composition as defined by claim 3, said at least one insoluble organic UV-screening agent comprising an aryl vinylene ketone compound having either of the following formulae (10) and (11):

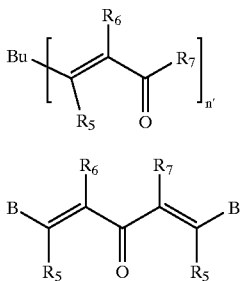

in which n'=1 or 2, B, in the formula (10) when n'=1 or in the formula (11), is an aryl radical selected from among the following formulae (a') to (d') or, in the formula (10) when n'=2, is a radical chosen from the following formulae (e') to (h'):

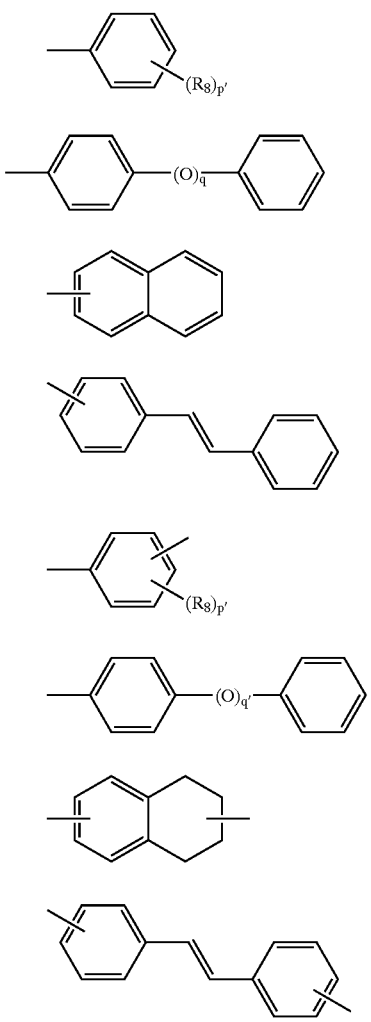

in which each of the $R_8$ symbols independently is an OH group, a halogen atom, a linear or branched $C_{1-6}$ alkyl radical optionally comprising a silicon atom, a linear or branched $C_{1-6}$ alkoxy radical optionally comprising a silicon atom, a linear or branched $C_{1-5}$ alkoxycarbonyl radical, or a linear or branched $C_{1-6}$ alkylsulfonamide radical optionally comprising a silicon atom or an amino acid functional group; p' is an integer ranging from 0 to 4, inclusive; q' is 0 or 1, $R_5$ is hydrogen or an OH group; $R_6$ is hydrogen, a linear or branched $C_{1-6}$ alkyl radical optionally comprising a silicon atom, a cyano group, a $C_{1-6}$ alkylsulfonyl group or a phenylsulfonyl group; $R_7$ is a linear or branched $C_{1-6}$ alkyl radical optionally comprising a silicon atom or a phenyl radical which can form a bicycle and which is optionally substituted by one or two $R_4$ radicals; or $R_6$ and $R_7$ can together form a monocyclic, bicyclic or tricyclic $C_{2-10}$ hydrocarbonaceous radical, optionally interrupted by one or more nitrogen, sulfur and oxygen atoms and which can comprise another carbonyl, and optionally substituted by a linear or branched $C_1$–$C_8$ alkylsulfonamide group, and optionally comprising a silicon atom or an amino acid functional group; provided that, when n'=1, $R_6$ and $R_7$ do not form a camphor nucleus.

27. The cosmetic/dermatological sunscreen composition as defined by claim 26, said at least one aryl vinylene ketone compound having the formula (10) in which n'=1.

28. The cosmetic/dermatological sunscreen composition as defined by claim 27, said at least one aryl vinylene ketone compound comprising a styryl ketone compound, a benzylidenecineole compound, a benzylidenechromanone compound, a benzylidenethiochromanone compound, a benzylidenequinuclidinone compound, a benzylidenecycloalkanone compound, a benzylidenehydantoin compound, a benzylideneindanone compound, a benzylidenetetralone compound, a benzylidenefuranone compound, a benzylidenebenzofuranone compound, a benzylideneindanedione compound, a benzylidenebenzothiofuranone compound, a benzylidenebarbituric compound, a benzylidenepyrazolone compound, a benzylideneimidazolone compound, a chalcone compound and/or a benzylidenone compound.

29. The cosmetic/dermatological sunscreen composition as defined by claim 28, said at least one aryl vinylene ketone compound comprising 1-(3,4-dimethoxyphenyl)-4,4-dimethylpent-1-en-3-one, 1,3, 3-trimethyl-5-(4-methoxybenzylidene)-2-oxa-bicyclo[2.2.2]octan-6-one, 3-(4-methoxybenzylidene)-2,3,4a, 8a-tetrahydrochromen-4-one, 3-(4-methoxybenzylidene)-2,3,4a,8a-tetrahydrochromen-4-thione, 4-methoxybenzylidene-1-azabicyclo[2.2.2]octan-3-one, 2-(4-methoxybenzylidene) cyclopentanone, 2-(4-methoxybenzylidene)cyclohexanone, 5-(3,4-dimethoxybenzylidene)imidazolidine-2,4-dione, 2-(4-methoxybenzylidene)indan-1-one, 2-(4-methoxybenzylidene)-3,4-dihydro-2H-naphthalen-1-one, 4-(4-methoxybenzylidene)-2,2,5,5-tetramethyldihydrofuran-3-one, 2-benzylidenebenzofuran-3-one, 2-(3,5-di(tertbutyl)-4-hydroxybenzylidene)indane-1,3-dione, 2-benzylidenebenzo[b]thiophen-3-one, 5-(4-methoxybenzylidene)-1,3-dimethylpyrimidine-2,4,6-trione, 4-(4-methoxybenzylidene)-5-methyl-2-phenyl-2,4-dihydropyrazol-3-one, 5-(4-methoxybenzylidene)-2-phenyl-3,5-dihydro-imidazol-4-one, 1-(2-hydroxy-4-methoxyphenyl)-3-phenylpropenone and/or 3-hydroxy-1-(2-hydroxy-4-methoxyphenyl)-3-phenylpropenone.

30. The cosmetic/dermatological sunscreen composition as defined by claim 26, said at least one aryl vinylene ketone compound having the formula (10) in which n'=2.

31. The cosmetic/dermatological sunscreen composition as defined by claim 30, said at least one aryl vinylene ketone compound comprising a phenylenebis(methylidenenorcamphor) compound, a phenylenebis (methylidenecamphor) compound, a phenylenebis(methylidenecamphor-sulfonamide) compound, a phenylenebis(methylidenecineole) compound, a phenylenebis(methylideneketo-tricyclodecane) compound, a phenylenebis(alkylene ketone) compound, a phenylenebis(methylidenefuranone) compound and/or a phenylenebis(methylidene-quinuclidinone) type.

32. The cosmetic/dermatological sunscreen composition as defined by claim 31, said at least one aryl vinylene ketone compound comprising 1,4-phenylenebis{3-methylidenebicyclo[2.2.1]heptan-2-one}, 1,4-phenylenebis{3-methylidene-1,7,7-trimethyl-bicyclo[2.2.1]heptan-2-one} or 1,3-phenylenebis-{3-methylidene-1,7,7-trimethylbicyclo[2.2.1]heptan-2-one}, 1,4-phenylenebis{3,3'-methylidenecamphor-10,10'-ethylsulfonamide or -(2-ethylhexyl)sulfonamide}, 1,4-phenylenebis{5-methylidene-3,3-dimethyl-2-oxa-bicyclo[2.2.2]octan-6-one}, 1,4-phenylenebis(octahydro-4,7-methano-6-inden-5-one), 1,4-phenylenebis(4,4-dimethylpent-1-en-3-one), 1,4-phenylenebis(4-methylidene-2,2,5,5-tetramethyl-dihydrofuran-3-one) and/or 1,4-phenylenebis{2-methylidene-1-azabicyclo[2.2.2]-octan-3-one}.

33. The cosmetic/dermatological sunscreen composition as defined by claim 26, said at least one aryl vinylene ketone compound comprising a bis(benzylidene)cycloalkanone compound and/or an y-pyrone compound.

34. The cosmetic/dermatological sunscreen composition as defined by claim 33, said at least one aryl vinylene ketone compound comprising 2,5-di(benzylidene)cyclopentanone and/or 2,6-bis(3,4-dimethoxyphenyl)pyran-4-one.

35. The cosmetic/dermatological sunscreen composition as defined by claim 3, said at least one insoluble organic UV-screening agent comprising a phenylenebis(benzoxazinone) compound having the following formula (12):

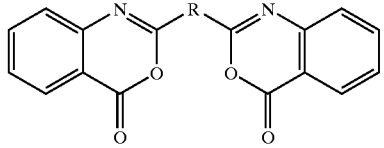

(12)

in which R is a divalent aromatic residue selected from among those of the following formulae (e") to (h"):

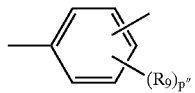

(e")

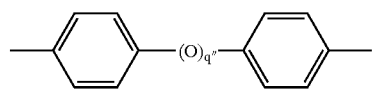

(f")

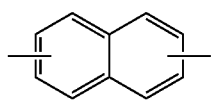

(g")

-continued

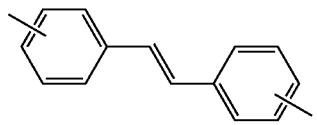

(h")

in which each of the $R_9$ radicals independently is an OH group, a halogen atom, a linear or branched $C_{1-6}$ alkyl radical optionally comprising a silicon atom, a linear or branched $C_{1-6}$ alkoxy radical optionally comprising a silicon atom, a linear or branched $C_{1-5}$ alkoxycarbonyl radical, or a linear or branched $C_{1-6}$ alkylsulfonamide group optionally comprising a silicon atom or an amino acid functional group; p" is an integer ranging from 0 to 4, inclusive; and q" is 0 or 1.

36. The cosmetic/dermatological sunscreen composition as defined by claim 35, comprising at least one insoluble compound of formula (12) selected from among 2,2'-p-phenylenebis(3,1-benzoxazin-4-one), 2,2'-(4,4'-biphenylene)bis(3,1-benzoxazin-4-one) and/or 2,2'-(2,6-naphthylene)bis(3,1-benzoxazin-4-one).

37. The cosmetic/dermatological sunscreen composition as defined by claim 3, said at least one insoluble organic UV-screening agent comprising a acrylonitrile amide, sulfonamide or carbamate compound having the following formula (13):

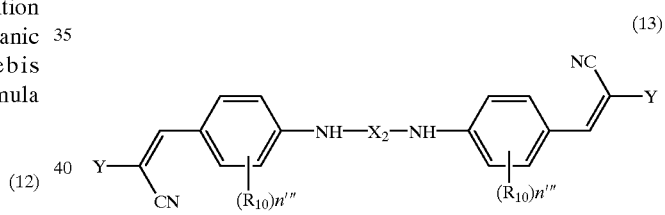

(13)

in which $R_{10}$ is a linear or branched $C_{1-8}$ alkyl radical; n'" is 0, 1 or 2, $X_2$ is a divalent radical of formula —(C=O)—$R_{11}$—(C=O)—, —$SO_2$—$R_{11}$—$SO_2$— or —(C=O)—O—$R_{11}$—O—(C=O)—; Y is a —(C=O)—$R_{12}$ or —$SO_2R_{13}$ radical; $R_{11}$ is a single bond or a linear or branched, divalent $C_1$–$C_{30}$ alkylene or $C_3$–$C_{30}$ alkenylene radical optionally substituted with one or more hydroxyl substituents and which can comprise, in the carbonaceous chain, one or more heteroatoms selected from among oxygen, nitrogen and silicon atoms; $R_{12}$ is an —$OR_{14}$ or —$NHR_{14}$ radical; $R_{13}$ is a linear or branched $C_1$–$C_{30}$ alkyl radical or a phenyl radical which is unsubstituted or substituted by $C_1$–$C_4$ alkyl or alkoxy radicals; $R_{14}$ is a linear or branched $C_1$–$C_{30}$ alkyl or $C_3$–$C_{30}$ alkenyl radical optionally substituted with one or more hydroxyl heteroatoms slected from among oxygen, nitrogen and silicon atoms; and isomers thereof.

38. The cosmetic/dermatological sunscreen composition as defined by claim 37, said at least one insoluble UV-screening agent comprising the dimer of 2-ethylhexyl 2-cyano-3-[4-(acetylamino)phenyl]acrylate having the formula:

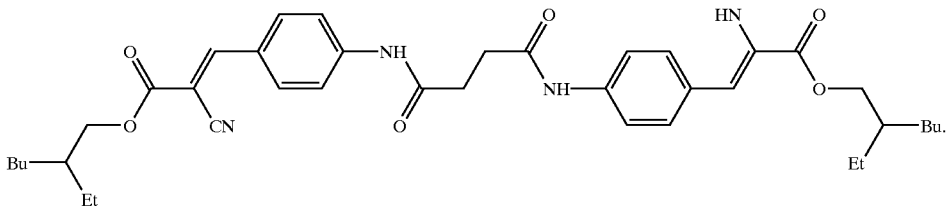

39. The cosmetic/dermatological sunscreen composition as defined by claim 1, said at least one insoluble UV-screening agent comprising a polyvalent metal salt of a sulfonic or carboxylic organic UV-screening agent.

40. The cosmetic/dermatological sunscreen composition as defined by claim 39, said at least one insoluble UV-screening agent comprising a polyvalent metal salt of sulfonated compound of benzylidenecamphor; a polyvalent metal salt of a sulfonated compound of benzimidazole; or a polyvalent metal salt of a cinnamic acid compound.

41. The cosmetic/dermatological sunscreen composition as defined by claim 1, said at least one insoluble UV-screening agent comprising a polyvalent metal or ammonium or substituted ammonium complex of a UV-A and/or UV-B organic screening agent.

42. The cosmetic/dermatological sunscreen composition as defined by claim 1, said at least one insoluble UV-screening agent comprising from about 1% to 10% by weight, with respect to the total weight thereof.

43. The cosmetic/dermatological sunscreen composition as defined by claim 42, said at least one insoluble UV-screening agent comprising from about 2% to 8% by weight, with respect to the total weight thereof.

44. The cosmetic/dermatological sunscreen composition as defined by claim 1, said at least one compound of formula (I) having the following formula (Ia):

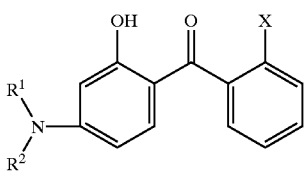

(Ia)

in which $R^1$ and $R^2$, which may be identical or different, are each a hydrogen atom or a $C_1$–$C_{12}$ alkyl radical, or together form, with the nitrogen atom to which they are bonded, a 5- or 6-membered heterocyclic ring member; X is $COOR^5$ or $CONR^6R^7$; $R^5$ is a hydrogen atom, a $C_1$–$C_{12}$ alkyl radical or a $C_3$–$C_6$ cycloalkyl radical; and the radicals $R^6$ and $R^7$, which may be identical or different, are each a hydrogen atom, a $C_1$–$C_{12}$ alkyl radical or a $C_5$–$C_6$ cycloalkyl radical.

45. The cosmetic/dermatological sunscreen composition as defined by claim 44, wherein formula (Ia), $R^1$ and $R^2$, which may be identical or different, are each a $C_1$–$C_4$ alkyl radical; $R^5$ is a $C_3$–$C_8$ alkyl radical; and $R^6$ and $R^7$, which may be identical or different, are each a $C_1$–$C_8$ alkyl radical.

46. The cosmetic/dermatological sunscreen composition as defined by claim 1, said at least one compound of formula (I) having the following formula (Ib):

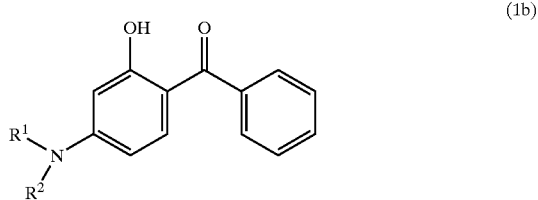

(Ib)

in which $R^1$ and $R^2$, which may be identical or different, are each a $C_1$–$C_{12}$ alkyl radical, or together form, with the nitrogen atom to which they are bonded, a 5- or 6-membered heterocyclic ring member.

47. The cosmetic/dermatological sunscreen composition as defined by claim 46, said at least one compound of formula (Ib) comprising 4-diethylamino-2-hydroxyphenyl phenyl ketone, and/or 4-pyrrolidino-2-hydroxyphenyl phenyl ketone.

48. The cosmetic/dermatological sunscreen composition as defined by claim 1, said at least one compound of formula (I) having the following formula (Ic):

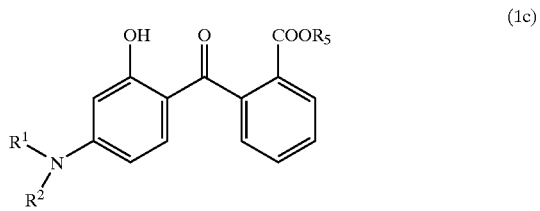

(Ic)

in which $R^1$ and $R^2$, which may be identical or different, are each a hydrogen atom, or a $C_1$–$C_8$ alkyl radical, or together form, with the nitrogen atom to which they are bonded, a 5- or 6-membered heterocyclic ring member; and $R^5$ is a hydrogen atom, a $C_1$–$C_{12}$ alkyl radical or a $C_3$–$C_6$ cycloalkyl radical.

49. The cosmetic/dermatological sunscreen composition as defined by claim 48, said at least one compound of formula (Ic) comprising 2-(4-pyrrolidino-2-hydroxybenzoyl)benzoic acid, methyl 2-(4-diethylamino-2-hydroxybenzoyl)benzoate, 2-ethylhexyl 2-(4-diethylamino-2-hydroxybenzoyl)-benzoate, cyclohexyl 2-(4-diethylamino-2-hydroxybenzoyl)-benzoate, n-hexyl 2-(4-diethylamino-2-hydroxybenzoyl)benzoate, 2-(4-dibutylamino-2-hydroxybenzoyl)benzoic acid, methyl 2-(4-dibutylamino-2-hydroxybenzoyl)benzoate and/or isobutyl 2-(4-dibutylamino-2-hydroxybenzoyl)benzoate.

50. The cosmetic/dermatological sunscreen composition as defined by claim 49, said at least one compound of formula (Ic) comprising n-hexyl 2-(4-diethyl-amino-2-hydroxybenzoyl)benzoate.

51. The cosmetic/dermatological sunscreen composition as defined by claim 1, said at least one amino-substituted 2-hydroxy-benzophenone compound comprising from 0.1% to 20% by weight, with respect to the total weight thereof.

52. The cosmetic/dermatological sunscreen composition as defined by claim 51, said at least one amino-substituted 2-hydroxybenzophenone compound comprising from 0.1% to 15% by weight, with respect to the total weight thereof.

53. The cosmetic/dermatological sunscreen composition as defined by claim 52, said at least one amino-substituted 2-hydroxybenzophenone compound comprising from 0.5% to 10% by weight, with respect to the total weight thereof.

54. The cosmetic/dermatological sunscreen composition as defined by claim 1, additionally comprising at least one soluble organic screening agent which is active in the UV-A and/or UV-B regions.

55. The cosmetic/dermatological sunscreen composition as defined by claim 54, said additional soluble organic UV screening agent or agents being selected from among anthranilates; cinnamic derivatives; dibenzoylmethane derivatives; salicylic derivatives; camphor derivatives; triazine derivatives; benzophenone derivatives, other than those of formula (I); β,β-diphenylacrylate derivatives; benzotriazole derivatives; benzalmalonate derivatives; benzimidazole derivatives; imidazolines; bisbenzoazolyl derivatives; p-aminobenzoic acid (PABA) derivatives; methylenebis (hydroxyphenylbenzotriazole) derivatives; screening polymers and screening silicones; dimers derived from α-alkylstyrene; and 4,4-diarylbutadienes.

56. The cosmetic/dermatological sunscreen composition as defined by claim 55, said soluble organic UV screening agent or agents being selected from among Ethylhexyl Salicylate, Octocrylene, Ethylhexyl Methoxycinnamate, Butyl Methoxydibenzoylmethane, Phenylbenzimidazole Sulfonic Acid, Benzophenone-3, Benzophenone-4, Benzophenone-5,4-Methylbenzylidene camphor, Disodium Phenyl Dibenzimidazole Tetrasulfonate, Anisotriazine, Ethylhexyl triazone, Diethylhexyl Butamido Triazone, 2,4,6-Tris(diisobutyl 4'-aminobenzalmalonate)-s-triazine, Drometrizole Trisiloxane, Methylenebis (benzotriazolyltetramethylbutyl-phenol), 1,1-dicarboxy(2, 2'-dimethylpropyl)-4,4-diphenylbutadiene, and mixtures thereof.

57. The cosmetic/dermatological sunscreen composition as defined by claim 1, additionally comprising coated or uncoated metal oxide pigments or nanopigments.

58. The cosmetic/dermatological sunscreen composition as defined by claim 57, said pigments or nanopigments comprising coated or uncoated titanium dioxide, zinc oxide, iron oxide, zirconium oxide or cerium oxide, and mixtures thereof.

59. The cosmetic/dermatological sunscreen composition as defined by claim 1, additionally comprising at least one agent for the artificial tanning and/or browning of the skin.

60. The cosmetic/dermatological sunscreen composition as defined by claim 1, additionally comprising at least one adjuvant or additive selected from among fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, or colorants.

61. The cosmetic/dermatological sunscreen composition as defined by claim 1, formulated as a nonionic vesicular dispersion, an O/W or W/O emulsion, a cream, a milk, a gel, a cream gel, a suspension, a dispersion, a powder, a solid tube, a foam or a spray.

62. The cosmetic/dermatological sunscreen composition as defined by claim 1, formulated as a makeup for the eyelashes, eyebrows or skin and provided in the anhydrous or aqueous, pasty or solid form, in the form of an emulsion, of a suspension or of a dispersion.

63. The cosmetic/dermatological sunscreen composition as defined by claim 1, formulated for the protection of the hair against ultraviolet rays and provided in the form of a shampoo, of a lotion, of a gel, of an emulsion, or of a nonionic vesicular dispersion.

64. A regime or regimen for photoprotecting human skin and/or hair against the deleterious effects of ultraviolet irradiation, comprising topically applying thereon an effective amount of a cosmetic/dermatological composition which comprises synergistically UV-$A_{PPD}$-enhancing amounts of (a) particulates of at least one insoluble organic UV-screening agent having a particle size ranging from 10 nm to 5 μm, and (b) at least one UV-screening amino-substituted 2-hydroxybenzophenone compound having the following structural formula (I):

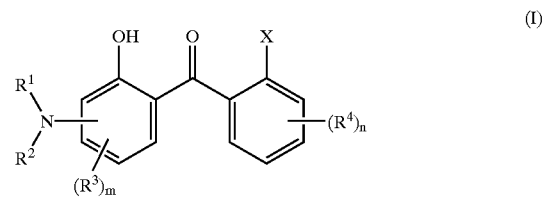

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a ($C_1$–$C_{20}$) alkoxycarbonyl radical, a $C_1$–$C_{12}$ alkylamino radical, a di($C_1$–$C_{12}$) alkylamino radical, an aryl radical or a heteroaryl radical which is optionally substituted, or a water-solubilizing substituent selected from among a carboxylate group, a sulfonate group or an ammonium residue; X is a hydrogen atom or a —$COOR^5$ or —$CONR^6R^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —$(YO)_o$—Z radical or an aryl radical; Y is —$(CH_2)_2$—, —$(CH_2)_3$—, —$(CH_2)_4$— or —$CH$—$CH_3$—$CH_2$—; Z is —$CH_2$—$CH_3$, —$CH_2CH_2CH_3$, —$CH_2$—$CH_2$—$CH_2$—$CH_3$ or —$CH(CH_3)$—$CH_3$; m is an integer ranging from 0 to 3; n is an integer ranging from 0 to 3; o is an integer ranging from 1 to 2, formulated into (c) a topically applicable, cosmetically/dermatologically acceptable vehicle, diluent or carrier therefor.

65. A method for synergistically enhancing the UV-A$_{PPD}$ of particulates of at least one insoluble organic UV-screening agent having an particle size ranging from 10 nm to 5 μm, comprising formulating therewith an effective amount of at least one amino-substituted 2-hydroxybenzophenone compound as defined in claim 1.

* * * * *